(12) United States Patent
Rodriguez-Navarro et al.

(10) Patent No.: US 10,010,370 B2
(45) Date of Patent: Jul. 3, 2018

(54) MAGNETIC CONTROL ASSEMBLIES AND SYSTEMS THEREFOR

(71) Applicant: LEVITA MAGNETICS INTERNATIONAL CORP., San Mateo, CA (US)

(72) Inventors: Alberto Rodriguez-Navarro, San Francisco, CA (US); Mariel Fabro, San Francisco, CA (US); Archana Nair, Eden Prairie, MN (US); Olgy Datto, Redwood City, CA (US)

(73) Assignee: Levita Magnetics International Corp., San Mateo, CA (US)

( * ) Notice: Subject to any disclaimer, the term of this patent is extended or adjusted under 35 U.S.C. 154(b) by 509 days.

(21) Appl. No.: 14/200,302

(22) Filed: Mar. 7, 2014

(65) Prior Publication Data

US 2014/0276941 A1    Sep. 18, 2014

Related U.S. Application Data

(60) Provisional application No. 61/785,489, filed on Mar. 14, 2013.

(51) Int. Cl.
*A61B 34/20* (2016.01)
*A61B 19/00* (2006.01)
(Continued)

(52) U.S. Cl.
CPC .......... *A61B 19/22* (2013.01); *A61B 17/0281* (2013.01); *A61B 34/70* (2016.02);
(Continued)

(58) Field of Classification Search
CPC ... A61B 34/73; A61B 2034/731; A61B 34/70; A61B 34/71; A61B 34/72; A61B 34/77;
(Continued)

(56) References Cited

U.S. PATENT DOCUMENTS 2,863,444 A    12/1958   Winsten
3,146,381 A     8/1964   Louis
(Continued)

FOREIGN PATENT DOCUMENTS

CA    2 748 471 A1    7/2010
CA    2733465 A1      9/2011
(Continued)

OTHER PUBLICATIONS

Corrected Notice of Allowability dated Apr. 5, 2016, for U.S. Appl. No. 14/019,404, filed Sep. 5, 2013, 3 pages.
(Continued)

*Primary Examiner* — Thaddeus Cox
(74) *Attorney, Agent, or Firm* — Cooley LLP

(57) ABSTRACT

Described here are devices and systems for applying an adjustable strength magnetic field to a magnetic device located within the body. In some variations, the devices may comprise a force modulation device comprising an adjustable shielding device. In other variations, the devices may comprise a force modulation device comprising a distance adjustment device. In some variations, the force modulation device may be adjusted by an automated control mechanism based on information from a sensor in the magnetic device.

4 Claims, 14 Drawing Sheets

(51) Int. Cl.
  *A61B 17/02* (2006.01)
  *A61B 34/00* (2016.01)
  *A61B 17/00* (2006.01)
  *A61B 90/00* (2016.01)
(52) U.S. Cl.
  CPC .............. *A61B 34/73* (2016.02); *A61B 90/03* (2016.02); *A61B 2017/00876* (2013.01)
(58) Field of Classification Search
  CPC .......... A61B 2034/733; A61B 17/0281; A61B 2017/00876; A61B 1/041; A61B 2034/732; A61B 2562/162; A61B 5/062; A61B 5/07; A61B 5/073
  See application file for complete search history.

(56) References Cited

U.S. PATENT DOCUMENTS

| | | |
|---|---|---|
| 3,674,014 A | 7/1972 | Tillander |
| 3,789,285 A | 1/1974 | Nishizawa |
| 4,364,377 A | 12/1982 | Smith |
| 4,380,999 A | 4/1983 | Healy |
| 4,971,067 A | 11/1990 | Bolduc et al. |
| 4,976,723 A | 12/1990 | Schad |
| 5,282,806 A | 2/1994 | Haber et al. |
| 5,304,183 A | 4/1994 | Gourlay et al. |
| 5,304,185 A | 4/1994 | Taylor |
| 5,307,805 A | 5/1994 | Byrne |
| 5,415,160 A | 5/1995 | Ortiz et al. |
| 5,449,361 A | 9/1995 | Preissman |
| 5,450,842 A | 9/1995 | Tovey et al. |
| 5,458,603 A | 10/1995 | Futch, Sr. |
| 5,458,693 A | 10/1995 | Codorniu |
| 5,465,711 A | 11/1995 | Moll et al. |
| 5,496,317 A | 3/1996 | Goble et al. |
| 5,499,986 A | 3/1996 | Dimarco |
| 5,529,568 A | 6/1996 | Rayman |
| 5,593,379 A | 1/1997 | Rayman |
| 5,595,562 A | 1/1997 | Grier |
| 5,654,864 A | 8/1997 | Ritter et al. |
| 5,665,100 A | 9/1997 | Yoon |
| 5,681,260 A | 10/1997 | Ueda et al. |
| 5,728,121 A | 3/1998 | Bimbo et al. |
| 5,733,292 A * | 3/1998 | Gustilo ................ A61B 17/025 606/86 R |
| 5,749,881 A | 5/1998 | Sackier et al. |
| 5,766,189 A | 6/1998 | Matsuno |
| 5,782,748 A | 7/1998 | Palmer et al. |
| 5,797,911 A | 8/1998 | Sherman et al. |
| 5,849,015 A | 12/1998 | Haywood et al. |
| 5,893,873 A | 4/1999 | Rader et al. |
| 6,015,414 A | 1/2000 | Werp et al. |
| 6,099,537 A | 8/2000 | Sugai et al. |
| 6,099,550 A | 8/2000 | Yoon |
| 6,123,657 A | 9/2000 | Ishikawa et al. |
| 6,126,647 A | 10/2000 | Posey et al. |
| 6,173,715 B1 | 1/2001 | Sinanan et al. |
| 6,212,419 B1 | 4/2001 | Blume et al. |
| 6,216,028 B1 | 4/2001 | Haynor et al. |
| 6,241,671 B1 | 6/2001 | Ritter et al. |
| 6,311,082 B1 | 10/2001 | Creighton, IV et al. |
| 6,315,709 B1 | 11/2001 | Garibaldi et al. |
| 6,330,467 B1 | 12/2001 | Creighton, IV et al. |
| 6,340,365 B2 | 1/2002 | Dittrich et al. |
| 6,358,196 B1 | 3/2002 | Rayman |
| 6,398,791 B1 | 6/2002 | Que et al. |
| 6,399,146 B1 | 6/2002 | Harris et al. |
| 6,401,723 B1 | 6/2002 | Garibaldi et al. |
| 6,440,133 B1 | 8/2002 | Beale et al. |
| 6,459,924 B1 | 10/2002 | Creighton, IV et al. |
| 6,464,710 B1 | 10/2002 | Foster |
| 6,488,615 B1 | 12/2002 | Mitchiner et al. |
| 6,523,919 B1 * | 2/2003 | Israelsen ................ A47B 63/00 312/310 |
| 6,537,196 B1 | 3/2003 | Creighton, IV et al. |
| 6,594,517 B1 | 7/2003 | Nevo |
| 6,630,879 B1 | 10/2003 | Creighton, IV et al. |
| 6,656,199 B1 | 12/2003 | Lafontaine |
| 6,677,752 B1 | 1/2004 | Creighton, IV et al. |
| 6,689,119 B1 | 2/2004 | Di Caprio et al. |
| 6,705,989 B2 | 3/2004 | Cuschieri et al. |
| 6,719,765 B2 | 4/2004 | Bonutti |
| 6,761,681 B2 | 7/2004 | Schmid et al. |
| 6,817,364 B2 | 11/2004 | Garibaldi et al. |
| 6,824,511 B1 | 11/2004 | Bell et al. |
| 6,916,314 B2 | 7/2005 | Schneider et al. |
| 7,017,584 B2 | 3/2006 | Garibaldi et al. |
| 7,094,245 B2 | 8/2006 | Adams et al. |
| 7,169,104 B2 | 1/2007 | Ueda et al. |
| 7,182,089 B2 | 2/2007 | Ries |
| 7,182,775 B2 | 2/2007 | De Guillebon et al. |
| 7,264,584 B2 | 9/2007 | Ritter et al. |
| 7,311,107 B2 | 12/2007 | Harel et al. |
| 7,313,429 B2 | 12/2007 | Creighton, IV et al. |
| 7,341,063 B2 | 3/2008 | Garbibaldi et al. |
| 7,344,553 B2 | 3/2008 | Opolski et al. |
| 7,416,335 B2 | 8/2008 | Munger |
| 7,429,259 B2 | 9/2008 | Cadeddu et al. |
| 7,431,726 B2 | 10/2008 | Spence et al. |
| 7,686,827 B2 | 3/2010 | Hushka |
| 7,691,103 B2 | 4/2010 | Fernandez et al. |
| 7,708,756 B2 | 5/2010 | Nobis et al. |
| 7,736,356 B2 | 6/2010 | Cooper et al. |
| 7,766,810 B2 | 8/2010 | Ohdaira |
| 7,769,427 B2 | 8/2010 | Shachar |
| 7,772,950 B2 | 8/2010 | Tunay |
| 7,774,046 B2 | 8/2010 | Werp et al. |
| 7,780,054 B2 | 8/2010 | Wales |
| 7,799,050 B2 | 9/2010 | Hensley et al. |
| 7,837,612 B2 | 11/2010 | Gill et al. |
| 7,850,591 B2 | 12/2010 | Spector |
| 7,963,903 B2 | 6/2011 | Ghiron et al. |
| 7,966,059 B2 | 6/2011 | Creighton, IV et al. |
| 8,038,612 B2 | 10/2011 | Paz |
| 8,043,290 B2 | 10/2011 | Harrison et al. |
| 8,057,472 B2 | 11/2011 | Walker et al. |
| 8,060,184 B2 | 11/2011 | Hastings et al. |
| 8,066,715 B2 | 11/2011 | Ducharme |
| 8,082,035 B2 | 12/2011 | Glukhovsky |
| 8,133,254 B2 | 3/2012 | Dumbauld et al. |
| 8,136,888 B2 | 3/2012 | Suzuki et al. |
| 8,137,268 B2 | 3/2012 | Van Lue |
| 8,157,149 B2 | 4/2012 | Olson et al. |
| 8,187,286 B2 | 5/2012 | Jugenheimer et al. |
| 8,197,494 B2 | 6/2012 | Jaggi et al. |
| 8,235,272 B2 | 8/2012 | Nicholas et al. |
| 8,241,322 B2 | 8/2012 | Whitman et al. |
| 8,246,529 B2 | 8/2012 | Riehl et al. |
| 8,252,021 B2 | 8/2012 | Boulnois et al. |
| 8,267,854 B2 | 9/2012 | Asada et al. |
| 8,301,226 B2 | 10/2012 | Csavoy et al. |
| 8,303,495 B2 | 11/2012 | Ducharme |
| 8,313,497 B2 | 11/2012 | Walberg et al. |
| 8,316,861 B2 | 11/2012 | Brewer et al. |
| 8,316,862 B2 | 11/2012 | Shapiro et al. |
| 8,333,695 B2 | 12/2012 | Cuschieri |
| 8,360,972 B2 | 1/2013 | Paz |
| 8,364,277 B2 | 1/2013 | Glukhovsky |
| 8,377,044 B2 | 2/2013 | Coe et al. |
| 8,382,754 B2 | 2/2013 | Odom et al. |
| 8,480,668 B2 | 7/2013 | Fernandez et al. |
| 8,491,626 B2 | 7/2013 | Roy et al. |
| 8,517,931 B2 | 8/2013 | Minnelli et al. |
| 8,518,057 B2 | 8/2013 | Walberg et al. |
| 8,556,919 B2 | 10/2013 | Aguirre et al. |
| 8,579,787 B2 | 11/2013 | Shapiro et al. |
| 8,585,685 B2 | 11/2013 | Hagg |
| 8,602,981 B2 | 12/2013 | Deutch |
| 8,608,773 B2 | 12/2013 | Tierney et al. |
| 8,623,011 B2 | 1/2014 | Spivey |
| 8,628,529 B2 | 1/2014 | Aldridge et al. |
| 8,636,762 B2 | 1/2014 | Whitman et al. |
| 8,637,818 B2 | 1/2014 | Balakin |

(56) References Cited

U.S. PATENT DOCUMENTS

| | | |
|---|---|---|
| 8,685,043 B2 | 4/2014 | Jugenheimer et al. |
| 8,758,394 B2 | 6/2014 | Zimmerling et al. |
| 8,764,769 B1 | 7/2014 | Rodriguez-Navarro et al. |
| 8,790,245 B2 | 7/2014 | Rodriguez Fernandez et al. |
| 8,820,602 B2 | 9/2014 | Walberg et al. |
| 8,827,891 B2 | 9/2014 | Roberts |
| 8,894,574 B2 | 11/2014 | Ellman |
| 8,926,656 B2 | 1/2015 | Palermo et al. |
| 8,968,356 B2 | 3/2015 | Mueller |
| 9,011,468 B2 | 4/2015 | Ketai et al. |
| 9,339,285 B2 | 5/2016 | Rodriguez-Navarro et al. |
| 9,844,391 B2 | 12/2017 | Rodriguez Fernandez et al. |
| 2002/0100486 A1 | 8/2002 | Creighton, IV et al. |
| 2003/0114731 A1 | 6/2003 | Cadeddu et al. |
| 2003/0125752 A1 | 7/2003 | Werp et al. |
| 2003/0208185 A1 | 11/2003 | Sheffer et al. |
| 2004/0050395 A1 | 3/2004 | Ueda et al. |
| 2004/0064153 A1 | 4/2004 | Creighton, IV et al. |
| 2004/0230100 A1 | 11/2004 | Shluzas |
| 2004/0249262 A1 | 12/2004 | Werp et al. |
| 2005/0080440 A1 | 4/2005 | Durgin et al. |
| 2005/0131390 A1 | 6/2005 | Heinrich et al. |
| 2005/0165449 A1 | 7/2005 | Cadeddu et al. |
| 2005/0220583 A1* | 10/2005 | Lutz ................... B66F 7/22 |
| | | 414/425 |
| 2005/0250988 A1 | 11/2005 | Ewers et al. |
| 2006/0015178 A1 | 1/2006 | Moaddeb et al. |
| 2006/0074448 A1 | 4/2006 | Harrison et al. |
| 2006/0079897 A1 | 4/2006 | Harrison et al. |
| 2006/0089633 A1 | 4/2006 | Bleich et al. |
| 2006/0149135 A1 | 7/2006 | Paz |
| 2006/0152309 A1 | 7/2006 | Mintchev et al. |
| 2006/0228421 A1* | 10/2006 | Seeney ................. A61N 2/12 |
| | | 424/489 |
| 2006/0241691 A1 | 10/2006 | Wilk |
| 2006/0247522 A1 | 11/2006 | Mcgee |
| 2006/0293566 A1 | 12/2006 | Brown |
| 2007/0016010 A1 | 1/2007 | Creighton, IV et al. |
| 2007/0027458 A1 | 2/2007 | Sixto, Jr. et al. |
| 2007/0043359 A1 | 2/2007 | Altarac et al. |
| 2007/0073102 A1 | 3/2007 | Matsuno et al. |
| 2007/0135678 A1 | 6/2007 | Suzuki |
| 2007/0135802 A1 | 6/2007 | Suzuki |
| 2007/0255273 A1* | 11/2007 | Fernandez ............ A61B 18/14 |
| | | 606/41 |
| 2007/0270629 A1 | 11/2007 | Charles |
| 2008/0097496 A1 | 4/2008 | Chang et al. |
| 2008/0108860 A1 | 5/2008 | Bell et al. |
| 2008/0134474 A1 | 6/2008 | Uryasov |
| 2008/0171907 A1 | 7/2008 | Long et al. |
| 2008/0243106 A1 | 10/2008 | Coe et al. |
| 2008/0249534 A1 | 10/2008 | Gruber et al. |
| 2008/0269779 A1 | 10/2008 | Cadeddu et al. |
| 2009/0005636 A1 | 1/2009 | Pang et al. |
| 2009/0043246 A1 | 2/2009 | Dominguez |
| 2009/0062772 A1 | 3/2009 | Wakeford et al. |
| 2009/0192344 A1 | 7/2009 | Bakos et al. |
| 2009/0267717 A1 | 10/2009 | Baskett |
| 2010/0036394 A1 | 2/2010 | Mintz et al. |
| 2010/0036399 A1 | 2/2010 | Viola |
| 2010/0081876 A1 | 4/2010 | Linenkugel et al. |
| 2010/0105984 A1* | 4/2010 | Brewer ............ A61B 1/00158 |
| | | 600/118 |
| 2010/0113872 A1 | 5/2010 | Asada et al. |
| 2010/0114126 A1 | 5/2010 | Neff |
| 2010/0145147 A1 | 6/2010 | Pinsky et al. |
| 2010/0160739 A1 | 6/2010 | Van Lue |
| 2010/0168523 A1 | 7/2010 | Ducharme |
| 2010/0174234 A1 | 7/2010 | Werp et al. |
| 2010/0193566 A1 | 8/2010 | Scheib et al. |
| 2010/0204727 A1 | 8/2010 | Dominguez |
| 2010/0217245 A1 | 8/2010 | Prescott |
| 2010/0268254 A1 | 10/2010 | Golden et al. |
| 2010/0298645 A1 | 11/2010 | Deutch |
| 2011/0040152 A1 | 2/2011 | Kim et al. |
| 2011/0054306 A1 | 3/2011 | Del Nido et al. |
| 2011/0087223 A1 | 4/2011 | Spivey |
| 2011/0087224 A1 | 4/2011 | Cadeddu et al. |
| 2011/0087249 A1 | 4/2011 | Rodriques et al. |
| 2011/0105848 A1 | 5/2011 | Sadovsky et al. |
| 2011/0121050 A1 | 5/2011 | Nicholas et al. |
| 2011/0130787 A1 | 6/2011 | Cinquin et al. |
| 2011/0184440 A1 | 7/2011 | Saldinger |
| 2011/0230726 A1* | 9/2011 | Viola ................... A61B 19/22 |
| | | 600/227 |
| 2011/0276941 A1 | 11/2011 | Oi |
| 2011/0283822 A1 | 11/2011 | Cadeddu et al. |
| 2011/0284014 A1 | 11/2011 | Cadeddu et al. |
| 2011/0285488 A1 | 11/2011 | Scott et al. |
| 2011/0295067 A1 | 12/2011 | Rodriguez Fernandez et al. |
| 2011/0313415 A1 | 12/2011 | Fernandez et al. |
| 2012/0016362 A1 | 1/2012 | Heinrich et al. |
| 2012/0035416 A1 | 2/2012 | Fernandez et al. |
| 2012/0065627 A1 | 3/2012 | Ghabrial et al. |
| 2012/0078292 A1 | 3/2012 | Banju |
| 2012/0085358 A1 | 4/2012 | Cadeddu et al. |
| 2012/0101488 A1 | 4/2012 | Aldridge et al. |
| 2013/0030462 A1 | 1/2013 | Keating et al. |
| 2013/0085341 A1 | 4/2013 | Nobis et al. |
| 2013/0110128 A1* | 5/2013 | Schostek ............ A61B 1/00158 |
| | | 606/130 |
| 2013/0123828 A1 | 5/2013 | Culmer et al. |
| 2013/0158523 A1 | 6/2013 | Bergs et al. |
| 2013/0158659 A1 | 6/2013 | Bergs et al. |
| 2013/0158660 A1 | 6/2013 | Bergs et al. |
| 2013/0226226 A1 | 8/2013 | Garrison et al. |
| 2013/0245356 A1 | 9/2013 | Fernandez et al. |
| 2013/0253275 A1 | 9/2013 | Ransden et al. |
| 2013/0289768 A1 | 10/2013 | Yeung et al. |
| 2014/0243586 A1 | 8/2014 | Rohaninejad et al. |
| 2014/0257370 A1 | 9/2014 | Taylor et al. |
| 2014/0277104 A1 | 9/2014 | Rodriguez-Navarro et al. |
| 2014/0336470 A1 | 11/2014 | Rodriguez Fernandez et al. |
| 2014/0350574 A1 | 11/2014 | Farritor et al. |
| 2015/0230801 A1 | 8/2015 | Rodriguez Fernandez et al. |
| 2016/0228138 A1 | 8/2016 | Rodriguez-Navarro et al. |
| 2016/0302811 A1 | 10/2016 | Rodriguez-Navarro et al. |

FOREIGN PATENT DOCUMENTS

| | | |
|---|---|---|
| CN | 2244381 Y | 1/1997 |
| CN | 101090672 A | 12/2007 |
| CN | 201079412 Y | 7/2008 |
| CN | 201091596 Y | 7/2008 |
| CN | 101534725 A | 9/2009 |
| CN | 102068288 A | 5/2011 |
| CN | 102355865 A | 2/2012 |
| DE | 42 12 430 A1 | 10/1993 |
| DE | 19534618 A1 | 3/1997 |
| DE | 10 2005 006 705 A1 | 8/2006 |
| EP | 1 797 823 A1 | 6/2007 |
| EP | 1 972 284 A2 | 9/2008 |
| EP | 2 366 357 A1 | 9/2011 |
| EP | 2 391 277 | 12/2011 |
| EP | 1 942 810 B1 | 8/2012 |
| EP | 2 595 548 | 5/2013 |
| JP | 09-192137 A | 7/1997 |
| JP | 2005-021576 A | 1/2005 |
| JP | 4320214 B2 | 8/2009 |
| JP | 2009-538699 A | 11/2009 |
| WO | WO-2005/004734 A1 | 1/2005 |
| WO | WO-2006/071120 A1 | 7/2006 |
| WO | WO-2007/142977 A2 | 12/2007 |
| WO | WO-2007/142977 A3 | 12/2007 |
| WO | WO-2008/039237 A1 | 4/2008 |
| WO | WO-2008/131128 A1 | 10/2008 |
| WO | WO-2009/019288 A2 | 2/2009 |
| WO | WO-2009/019288 A3 | 2/2009 |
| WO | WO-2009/070743 A1 | 6/2009 |
| WO | WO-2010/089635 A1 | 8/2010 |
| WO | WO-2011/091483 A1 | 8/2011 |
| WO | WO-2012/010910 A1 | 1/2012 |
| WO | WO-2014/159023 A1 | 10/2014 |

(56) References Cited

FOREIGN PATENT DOCUMENTS

| WO | WO-2014/163872 A1 | 10/2014 |
| WO | WO-2015/112645 A1 | 7/2015 |
| WO | WO-2016/168380 A1 | 10/2016 |

OTHER PUBLICATIONS

Dominguez. "Colecistectomia con un trocar asistida por imanes de neodimio. Reporte de un caso." *Asociacion Mexicana de Cirugia Endo.* vol. 8. No. 4. 2007. pp. 172-176.—(with English Abstract).
Final Office Action dated Sep. 16, 2016, for U.S. Appl. No. 14/704,828, filed May 5, 2015, 10 pages.
Final Office Action dated Jan. 25, 2016, for U.S. Appl. No. 14/337,082, filed Jul. 21, 2014, 9 pages.
International Search Report dated Jul. 30, 2014, for PCT Application No. PCT/US2014/021537, filed on Mar. 7, 2014, 2 pages.
International Search Report for International Application No. PCT/IB2009/054307 dated Feb. 8, 2010 (with English Translation).
International Search Report dated Jul. 18, 2014, for PCT Application No. PCT/US2014/018307, filed on Feb. 25, 2014, 4 pages.
Non-Final Office Action dated May 21, 2013 for U.S. Appl. No. 13/132,185, filed Aug. 17, 2011, 18 pages.
Non-Final Office Action dated Jul. 21, 2016, for U.S. Appl. No. 14/337,082, filed Jul. 21, 2014, 9 pages.
Non-Final Office Action dated Jul. 13, 2015, for U.S. Appl. No. 14/337,082, filed Jul. 21, 2014, 10 pages.
Non-Final Office Action dated Jan. 25, 2016, for U.S. Appl. No. 14/704,828, filed May 5, 2015, 9 pages.
Non-Final Office Action dated Jul. 14, 2015, for U.S. Appl. No. 14/704,828, filed May 5, 2015, 10 pages.
Notice of Allowance dated Mar. 14, 2014, for U.S. Appl. No. 13/132,185, filed Aug. 17, 2011, 7 pages.
Notice of Allowance dated Mar. 14, 2016, for U.S. Appl. No. 14/019,404, filed Sep. 5, 2013, 7 pages.
Written Opinion of the International Searching Authority dated Jul. 30, 2014, for PCT Application No. PCT/US2014/021537, filed on Mar. 7, 2014, 5 pages.
Written Opinion of the International Searching Authority for International Application No. PCT/IB2009/054307 dated Feb. 8, 2010 (with English Translation).
Written Opinion of the International Searching Authority dated Jul. 18, 2014, for PCT Application No. PCT/US2014/018307, filed on Feb. 25, 2014, 5 pages.
Extended European Search Report dated Jul. 20, 2016, for EP Application No. 14 778 895.4, filed on Feb. 25, 2014, 7 pages.
International Search Report dated May 4, 2015, for PCT Application No. PCT/US2015/012319, filed on Jan. 21, 2015, 2 pages.
International Search Report dated Aug. 22, 2016, for PCT Application No. PCT/US2016/027390, filed on Apr. 13, 2016, 4 pages.
Non-Final Office Action dated Oct. 24, 2013, for U.S. Appl. No. 14/019,370, filed Sep. 5, 2013, 7 pages.
Non-Final Office Action dated Oct. 22, 2015, for U.S. Appl. No. 14/019,404, filed Sep. 5, 2013, 6 pages.
Notice of Allowance dated Feb. 14, 2014, for U.S. Appl. No. 14/019,370, filed Sep. 5, 2013, 7 pages.
Wikipedia (2015). "Stainless Steel," retrieved from https://en.wikipedia.org/wiki/Stainless_steel, 13 pages.
Written Opinion of the International Searching Authority dated May 4, 2015, for PCT Application No. PCT/US2015/012319, filed on Jan. 21, 2015, 5 pages.
Written Opinion of the International Searching Authority dated Aug. 22, 2016, for PCT Application No. PCT/US2016/027390, filed on Apr. 13, 2016, 9 pages.
Extended European Search Report dated Dec. 20, 2016, for EP Application No. 09 839 564.3, filed on Oct. 1, 2009, 11 pages.
Non-Final Office Action dated May 3, 2017, for U.S. Appl. No. 14/704,828, filed May 5, 2015, 8 pages.
Non-Final Office Action dated Jul. 24, 2017, for U.S. Appl. No. 15/098,262, filed Apr. 13, 2016, 9 pages.
Notice of Allowance dated May 3, 2017, for U.S. Appl. No. 14/337,082, filed Jul. 21, 2014, 7 pages.
Extended European Search Report dated Sep. 27, 2017, for EP Application No. 15 741 055.6, filed on Jan. 21, 2015, 9 pages.
Notice of Allowance dated Aug. 25, 2017, for U.S. Appl. No. 14/337,082, filed Jul. 21, 2014, 7 pages.
Notice of Allowance dated Jan. 19, 2018, for U.S. Appl. No. 14/704,828, filed May 5, 2015, 7 pages.

* cited by examiner

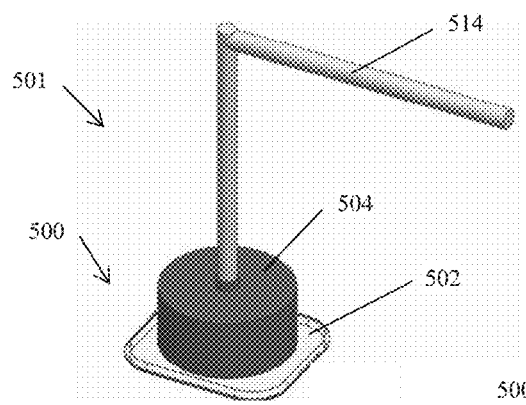
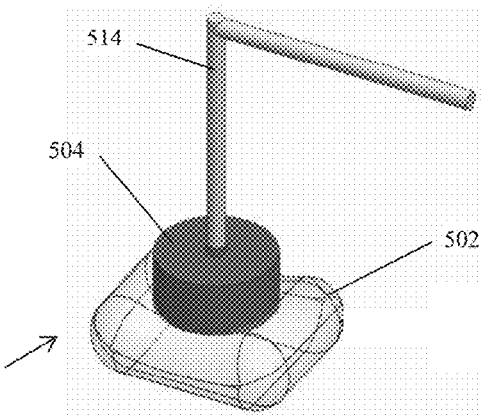
FIG. 5A
FIG. 5B
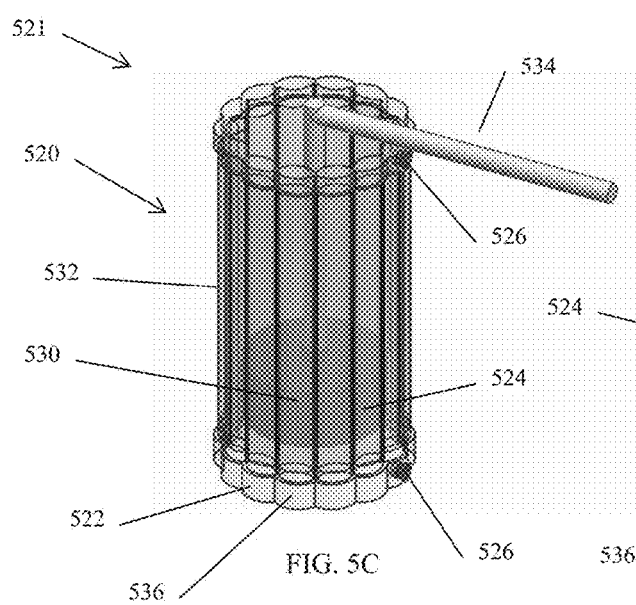
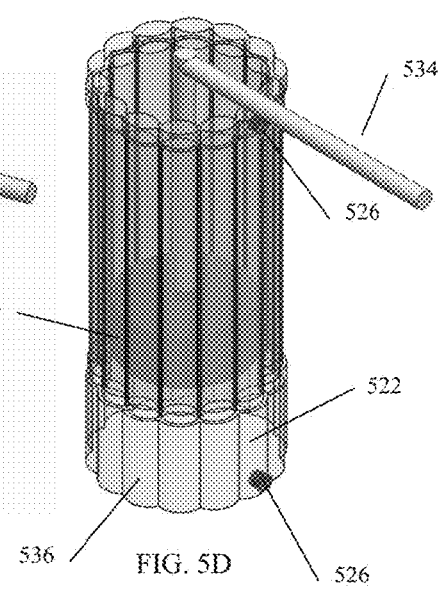
FIG. 5C
FIG. 5D

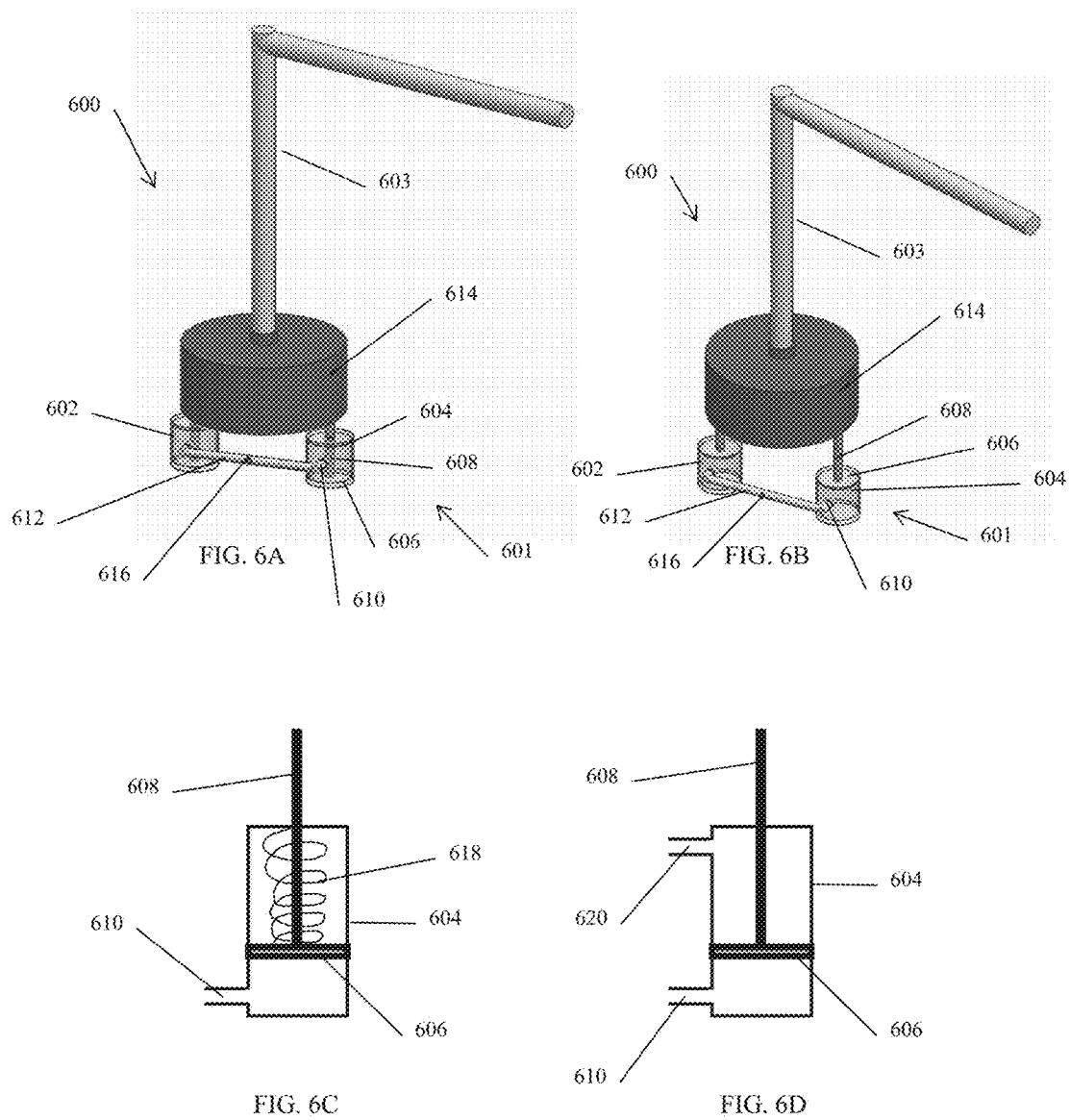

MAGNETIC CONTROL ASSEMBLIES AND SYSTEMS THEREFOR

CROSS-REFERENCE TO RELATED APPLICATIONS

This application claims priority to U.S. Provisional Application Ser. No. 61/785,489, filed on Mar. 14, 2013, and titled "MAGNETIC CONTROL ASSEMBLIES AND SYSTEMS THEREFOR," the content of which is hereby incorporated in its entirety.

FIELD

This invention relates generally to devices, systems, and methods for remotely manipulating instruments and tissue using an external magnet assembly.

BACKGROUND

Laparoscopic surgery is typically performed through one or more small incisions in a patient's body, which minimizes tissue damage and blood loss as compared to traditional surgery, and in turn decreases patient recovery time. Long, thin instruments are inserted into the body, which typically have a mechanical tool such as forceps or scissors attached at the distal end of the instrument. Despite laparoscopy's advantages over traditional surgery, its benefits are still limited by the small working envelopes surrounding each instrument. In order to change instrument position and to improve visibility and efficiency, surgeons must create multiple incisions. Methods for laparoscopy that require fewer ports to reduce the invasiveness and recovery time of the patient would therefore be desirable.

BRIEF SUMMARY

Described here are devices, systems, and methods for adjusting the strength of a magnetic field applied to a magnetic device located within the body. In some variations, the systems may comprise a magnetic device configured to be positioned in a body of a patient and a magnetic control assembly. The magnetic control assembly may comprise a magnet configured to generate a magnetic field and apply a magnetic force to the magnetic device. The magnetic control assembly may further comprise a force modulation device configured to alter a magnitude of the magnetic force applied by the magnet. In some variations, the magnetic control assembly may comprise a mounting device.

The force modulation device may be any suitable device, as described here. In some variations, the force modulation device comprises a controller, and may be configured to automatically alter the magnitude of the force applied by the magnet in response to information measured by a sensor. In some of these variations, the sensor may be carried by the magnetic device, and may comprise a magnetometer and/or pressure sensor. In some variations, the force modulation device may be configured to modify the magnetic field produced by the magnet. In some of these variations, the adjustable shielding device may comprise an iris assembly. The iris assembly may comprise a plurality of leaflets formed from a magnetic shielding material. In other variations, the adjustable shielding device may comprise one or more plates formed from a magnetic shielding material. In some of these variations, the one or more plates may be moveable relative to the magnet. Additionally or alternatively, the force modulation device may comprise a distance adjustment device configured to modify a distance between the magnet and the magnetic device. In some of these variations, the distance adjustment device may comprise an inflatable member. In other variations, the distance adjustment device may comprise a pneumatic piston assembly. In still other variations, the distance adjustment device may comprise a linkage assembly.

Also described here are methods for performing minimally invasive surgery. The methods generally comprise positioning a magnetic device within a body of a patient and positioning a magnetic control assembly externally of the body. The magnetic control assembly may comprise a magnet configured to generate a magnetic field and apply a magnetic force to the magnetic device. The magnetic control assembly may also comprise a force modulation device, wherein the force modulation device is configured to alter a magnitude of the magnetic force applied by the magnet. The magnetic control assembly may apply the magnetic force to the magnetic device to manipulate the magnetic device. The methods may further comprise adjusting the magnetic force applied to the magnetic device using the force modulation device. The magnetic force may be adjusted using any of the force modulation devices described here. In some variations, the force modulation device may comprise a controller, and may be configured to automatically adjust the force based on information received from a sensor. In some variations, the sensor may be carried by the magnetic device placed in the body.

BRIEF DESCRIPTION OF THE DRAWINGS

FIGS. 5A-5D depict perspective views of variations of the magnetic control assemblies described here having distance adjustment devices.

FIGS. 6A-6B depict perspective views of another illustrative magnetic control assembly having a distance adjustment device. FIGS. 6C-6D depict cross-sectional side views of variations of the distance adjustment device of FIGS. 6A-6B.

8B depicts a perspective view of a portion of a magnetic control assembly as described here.

DETAILED DESCRIPTION

Described here are devices and systems for remote manipulation of tissue during minimally-invasive procedures such as laparoscopic surgery. Generally, the systems comprise a magnetic device and a magnetic control assembly. Generally, the magnetic device is configured to be placed within a patient's body, and in some instances may be configured to couple to tissue within the body. The magnetic control assembly may be configured to be placed outside a patient's body and to produce a magnetic field. The magnetic field produced by the magnetic control assembly may provide one or more forces to the magnetic device to control the position of the magnetic device. The magnetic control assembly may comprise at least one magnet configured to generate a magnetic field and at least one force modulation device. The force modulation device may control the magnitude of the force applied to the magnetic device, as will be described in more detail below. In some embodiments, the force modulation device may comprise an adjustable shielding device, which may be configured to alter the magnetic field produced by the magnetic control assembly. Additionally or alternatively, the force modulation device may be configured to control a distance between the magnetic device and at least one magnet of the magnetic control assembly, which in turn may modulate the force applied to the magnetic device by the magnetic control assembly. In yet other embodiments, the force modulation device may be configured to both alter the magnetic field produced by the magnetic control assembly and control the distance between the magnetic control assembly and the magnetic device.

Figure 9A:
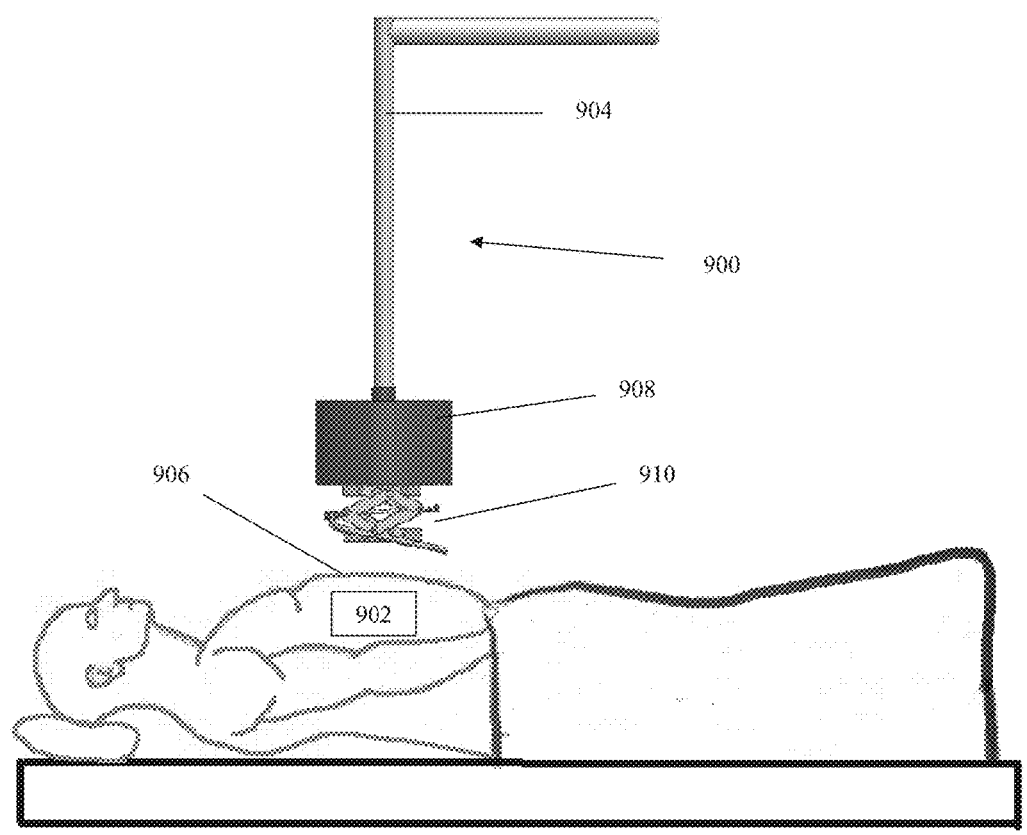
FIG. 9A shows a schematic of a variation of the systems described here.
Figure 9B:
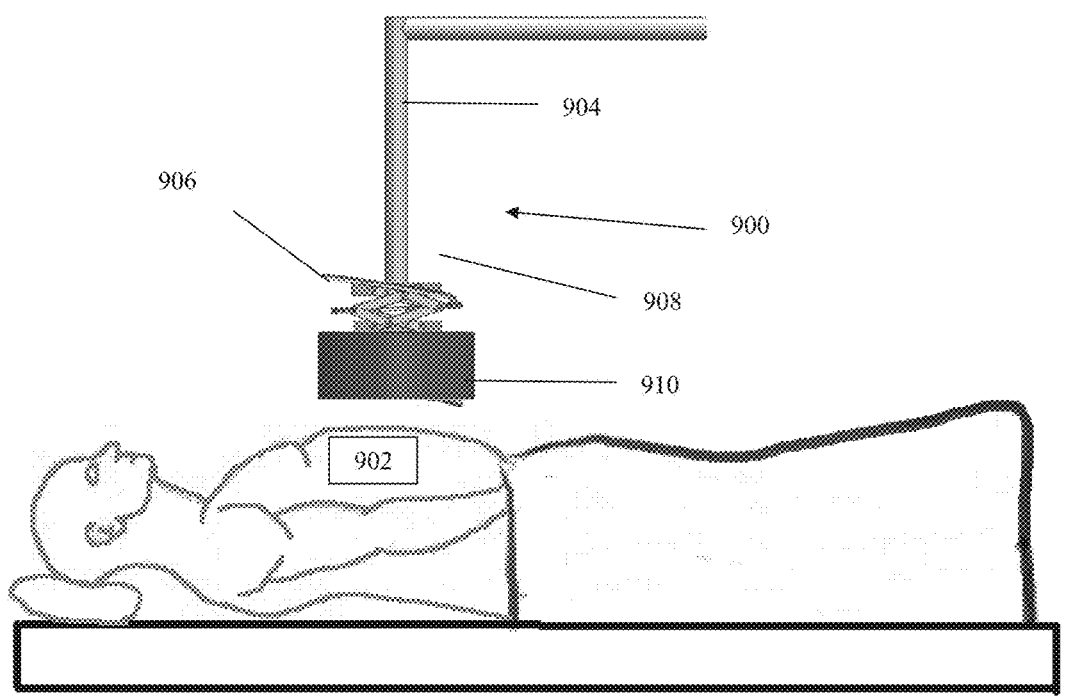
FIG. 9B shows a schematic of another variation of the systems described here.

FIGS. 9A and 9B shows illustrative variations of the systems described here. As shown there, the system may comprise a magnetic control assembly (900) and a magnetic device (902). The magnetic device (902) may be introduced into a patient's body, and may be releasably connected to tissue (not shown) (e.g., a gallbladder, an appendix, or the like) therein. The magnetic control assembly (900) may be positioned externally of the body, and may apply a magnetic field to the magnetic device (902), which may manipulate or move the magnetic device (902). For example, the magnetic control assembly (900) may raise the magnetic device (902) toward an abdominal wall (906), which in turn may lift the engaged tissue toward the abdominal wall and provide traction to the tissue or otherwise expose nearby tissue during a surgical procedure. In some variations, the magnetic assembly (900) may be mounted to a wall, ceiling, bed, cart, or other structure using a mounting device (904). Additionally, in some variations the magnetic assembly (900) may comprise a magnet (908) and a force modulation device (910). In some variations, as shown in FIG. 9A, the force modulation device (910) may be located between the magnet (908) and the abdominal wall (906). In other variations, as shown in FIG. 9B, the force modulation device (910) may be located between the magnet (908) and the mounting device (904). Examples of each of these devices will be described in more detail below.

Magnetic Device

As mentioned above, the systems described here may comprise a magnetic device configured to be inserted into a patient. The magnetic device may be configured for insertion into the patient during a minimally-invasive procedure, such as a laparoscopic operation. Accordingly, the magnetic device may be sized such that it may fit through a laparoscopic port (e.g., a 10 mm port or the like) or another incision formed in the body. In some instances, the magnetic device may be introduced into the abdominal cavity via an incision or port in the abdominal wall. The magnetic devices described here are typically configured to releasably connect to tissue. For example, the magnetic device may comprise a clip, grasper, fastener, or the like, and may be configured to connect to any suitable tissue. For example, when placed in the abdominal cavity, the magnetic device may be connected to an appendix, a gallbladder, or the like. In some variations, the magnetic device may be inserted and positioned with the help of one or more delivery devices. Examples of magnetic devices suitable for use with the systems described here are described in U.S. patent application Ser. No. 13/132,185, filed on Aug. 17, 2011 and titled "Remote Traction and Guidance System for Mini-Invasive Surgery," the contents of which are hereby incorporated by reference in their entirety.

Generally, the magnetic device is at least partially formed from one or more metallic or magnetic materials that may be attracted to a magnetic field, such that the magnetic device may be manipulated by magnetic fields produced by the magnetic control assembly. In some instances, the magnetic device may comprise one or more permanent magnets or electromagnets which may be configured to generate a magnetic field. The electromagnets may be selectively activated to generate a magnetic field. Additionally or alternatively, the magnetic device may comprise one or more ferromagnetic materials, which may become temporarily magnetized in the presence of a magnetic field. Suitable magnetic and ferromagnetic materials include, but are not limited to, rare-earth magnets (e.g., samarium-cobalt magnets, neodymium magnets), cobalt, gadolinium, iron, nickel, alnico alloys, ferrites, alloys thereof, combinations thereof, and the like.

In some variations, the magnetic device may be configured to provide feedback to the magnetic control assembly, and this feedback may be used by the magnetic control assembly to modulate the force applied to the magnetic device. In some of these variations, the magnetic device may comprise at least one sensor. In some variations, the magnetic device may comprise a magnetometer configured to measure the strength of the magnetic fields applied to magnetic device. In these variations, the magnetometer may comprise a scalar magnetometer configured to measure a total strength of the magnetic field applied thereto or may comprise a vector magnetometer configured to measure the strength of a magnetic field in a particular direction. In some instances, a magnetic device may comprise a plurality of vector magnetometers configured to measure the strength of a magnetic field in multiple directions (e.g., along two axes, along three axes, or the like).

Additionally or alternatively, a magnetic device may comprise a pressure sensor configured to measure pressure applied to one or more surfaces of the magnetic device. For example, when the magnetic device is pulled against an abdominal wall of a patient, the pressure sensor may be configured to measure the pressure between the magnetic device and the abdominal wall. It may be desirable to limit this pressure, as too much pressure applied to the abdominal wall may block blood flow thereto and possibly cause tissue necrosis. The magnetic devices may comprise any combination of pressure sensors and magnetometers. When a magnetic device comprises at least one sensor, the magnetic device may be configured to communicate data from the sensor or sensors to the magnetic control assembly. In some variations, the magnetic device may be configured to communicate this data wirelessly. Additionally or alternatively, the magnetic device may be configured to produce one or more signals which may be used by the magnetic control assembly to determine a relative positioning between the magnetic device and the magnetic control assembly.

Magnetic Control Assembly

Figure 8A:
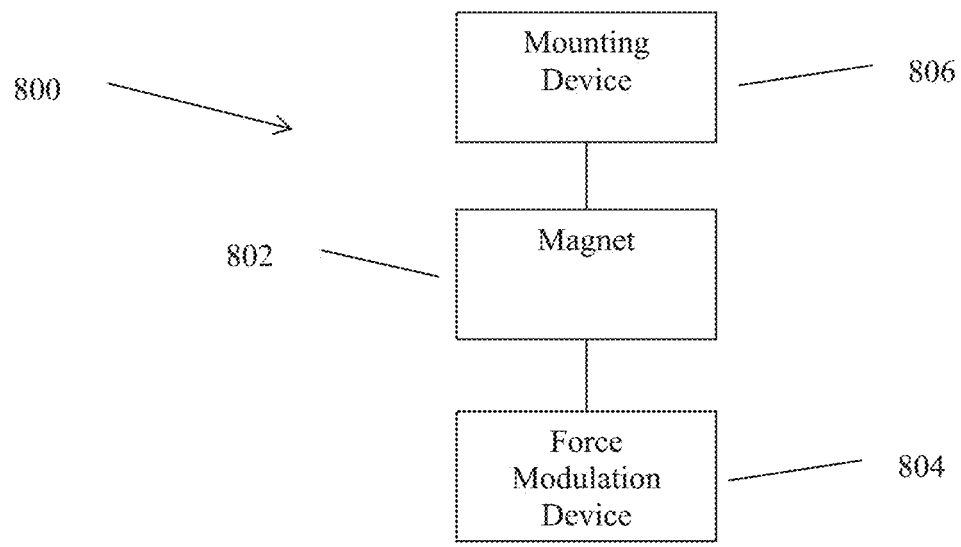
FIG. 8A depicts a block diagram of an illustrative variation of the magnetic control assemblies described here. FIG.
Figure 8B:
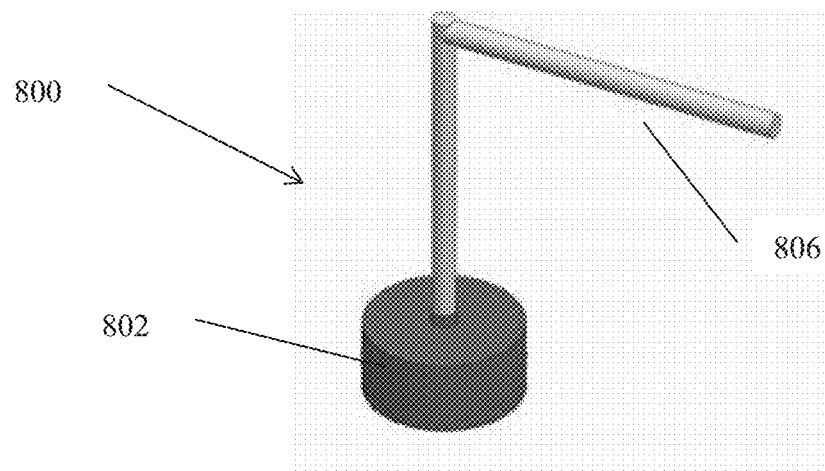
FIG. 8C depicts a block diagram of another illustrative variation of the magnetic control assemblies described here.
Figure 8C:
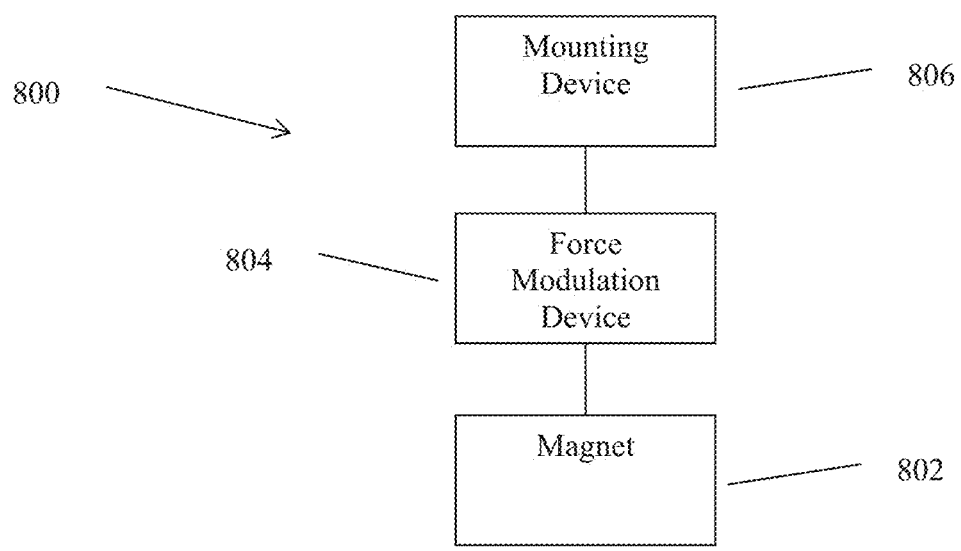

As mentioned above, the systems described here may comprise a magnetic control assembly configured to remotely manipulate a magnetic device located within the patient. FIGS. 8A and 8C depict block diagrams of variations of magnetic control assemblies as described here. As shown there, the magnetic control assembly (800) may comprise a magnet (802) and a force modulation device (804). In some variations, the magnetic control assembly (800) may further comprise a mounting device (806). As shown in FIG. 8A, in some variations the magnet (802) may be attached to the mounting device (806). In other variations, as shown there in FIG. 8C, the force modulation device (804) of the magnetic control assembly (800) may be located between the mounting device (806) and the magnet (802).

The magnet (802) may be configured to generate a magnetic field, such that when the magnetic control assembly (800) is positioned near a patient, the magnetic field may be generated inside the patient. This magnetic field may apply a force to and manipulate a magnetic device positioned in the body (e.g., within the abdomen). In some variations, the magnet (802) may comprise one or more permanent magnets and/or one or more electromagnets, which may be formed from one or more of the materials described above. The magnet (802) may comprise any number of individual magnets, which in some instances may be formed in an array. The magnet (802) may have any suitable size and shape, such as cylindrical shape having a circular, oval, or semi-circle cross-section, a bar magnet having a rectangular or triangular cross section, a spherical magnet, or the like.

As mentioned above, in some variations the magnetic control assembly (800) may comprise a mounting device (806). For example, FIG. 8B shows a perspective view of a portion of the magnetic control assembly (800) including the mounting device (806) and the magnet (802) (the force modulation device (804) is not illustrated in this figure). Generally, the mounting device (806) may be configured to mount the magnetic control assembly (800) to one or more structures (e.g., a wall, ceiling, an operating table, or the like). In some instances, the mounting device (806) may be further configured to counterbalance the weight of the magnet (802) and the force modulation device (804), such that the magnet (802) and the force modulation device (804) may be moveably suspended by the mounting device (806). With the magnetic control assembly (800) suspended by the mounting device (806), an operator may move the magnet (802) and/or force modulation device (804). Additionally or alternatively, the force modulation device (804) may alter the positioning of the magnet (802), as will be described below. In some variations, the position of the mounting device (806) may be temporarily locked to fix the positions of the magnet (802) and/or force modulation device (804).

In other instances, the mounting device (806) may be temporarily fixed relative to the one or more structures to which it is attached (e.g., a wall, ceiling, an operating table, or the like as mentioned above), and the force modulation device (804) may move the magnet (802) relative to the mounting device (806) (e.g., in variations where the force modulation device (804) is positioned between the magnet (802) and the mounting device (806)).

The magnetic control assemblies described here generally comprise a force modulation device. The force modulation device (e.g., force modulation device (804) shown in FIG. 8A) may be configured to modulate the strength of the magnetic field applied to a magnetic device positioned in the body. As mentioned above, in some instances it may be desirable to suspend a magnetic device against a tissue wall (e.g., the abdominal wall) while limiting the force that the magnetic device applies to the tissue wall. Accordingly, by modulating the strength of the magnetic field applied to the magnetic device, the magnetic control assembly may control the force applied to the magnetic device, which in turn may control the pressure applied by the magnetic device to the tissue wall. In some variations, the magnetic control assembly may comprise force modulation device that comprises an adjustable shielding device, which may alter the magnetic field produced by the magnet of the assembly. In other variations, the force modulation device may comprise a distance adjustment device, which may alter the distance between the magnet of the assembly and a magnetic device positioned in the body. In still other variations, the force modulation device may comprise an adjustable shielding device that is also configured to alter the distance between the magnet of the assembly and a magnetic device positioned in the body. In some embodiments, the force modulation device may be controlled by an automated feedback loop, as will be described in more detail below.

Adjustable Shielding Devices

In variations of the magnetic assemblies described here where the force modulation device comprises an adjustable shielding device, the adjustable shielding device generally comprises one or more shielding members that may alter the magnetic field produced by a magnet of the magnetic assembly. For example, the shielding member may comprise a magnetic shielding material such as one or more high magnetic permeability metal alloys (e.g., a Permalloy alloy or mu-metal alloy, or the like), which may act as a shield against a magnetic field produced by a magnet of the magnetic control assembly. When a shielding member is positioned between a magnet of the magnetic control assembly and a magnetic device positioned in a patient, the shielding member may reduce the strength of the magnetic field that reaches the magnetic device. Generally, the larger the area of a magnet that is shielded by a shielding member, the greater the reduction in the strength of the magnetic field reaching the device. Accordingly, the adjustable shielding devices described here may be configured to adjust the amount of shielding provided by the force modulation device, which in turn may modulate the magnetic field applied to the magnetic device.

Figure 1A:
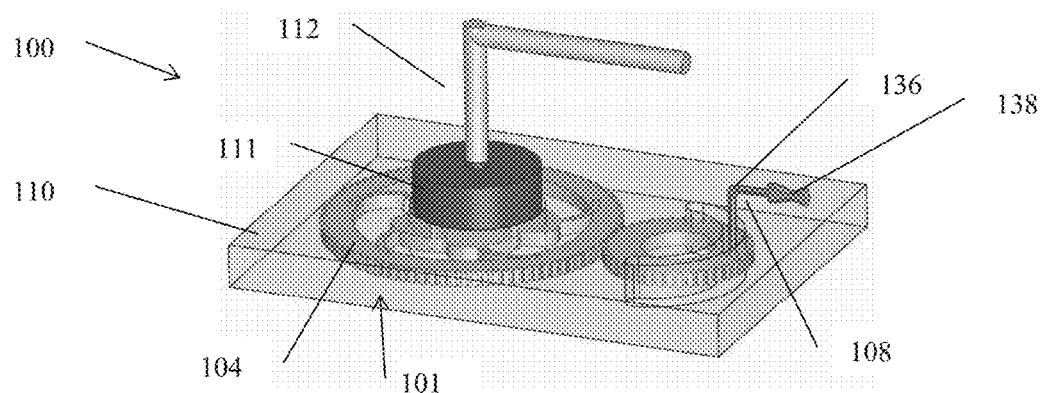
FIG. 1A depicts a perspective view of an illustrative magnetic control assembly having a shielding device.

For example, FIGS. 1A-1D depict one variation of a magnetic control assembly (100) having a force modulation device that comprises an adjustable shielding device (101). Specifically, FIG. 1A depicts a perspective view of the magnetic control assembly (100). As shown there, the magnetic control assembly (100) may comprise a magnet (111), a mounting device (112), and a force modulation device comprising an adjustable shielding device (101). The adjustable shielding device (101) may be connected to the magnet (111), which in turn may be connected to a mounting device (112) (which may connect the magnetic control assembly (100) to a wall, ceiling, bed, or other structure, such as discussed above). The adjustable shielding device (101) may be connected to the magnet (111), which in turn may be connected to a mounting device (112) (which may connect the magnetic control assembly (100) to a wall, ceiling, bed, or other structure, such as discussed above). The adjustable shielding device (101) may comprise an iris assembly configured to adjustably shield the magnet (111), as will be discussed in more detail below. Some or all of the components of the adjustable shielding device (101) may be positioned in a housing (110). Additionally, in some variations the adjustable shielding device (101) may comprise a control (108) configured to adjust the amount of shielding provided by the adjustable shielding device (101).

Figure 1B:
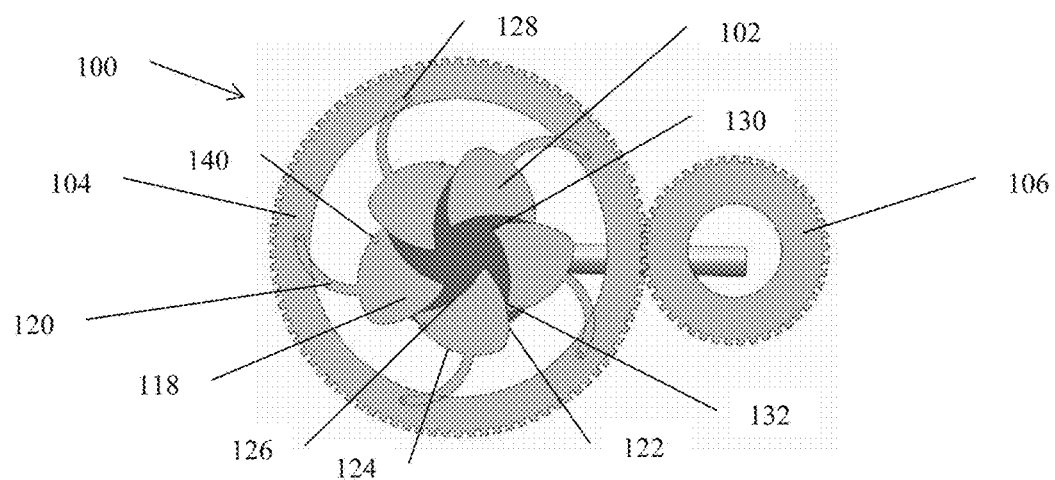
FIG. 1B shows a bottom view and FIGS. 1C and 1D depict perspective views, respectively, of the magnetic control assembly of FIG. 1A.
Figures 1C, 1D:
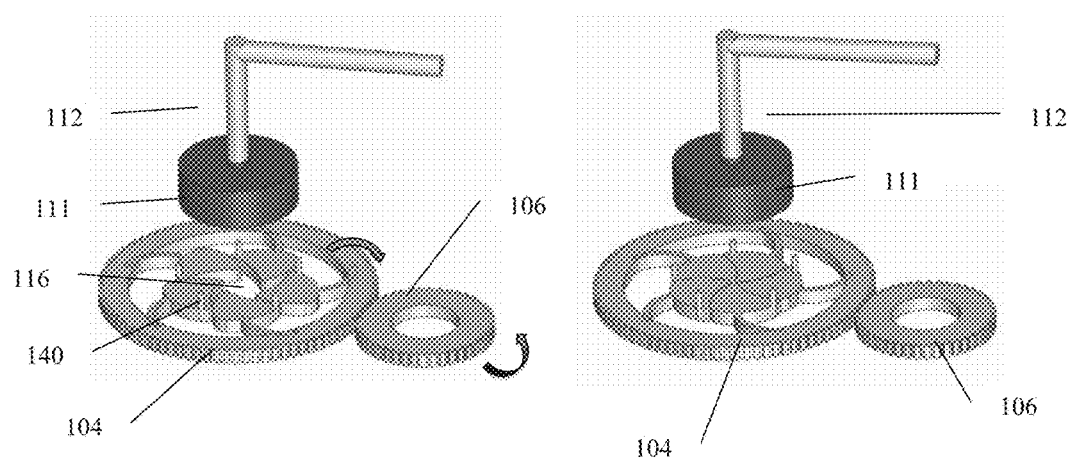

FIG. 1B shows a bottom view of the magnetic control assembly (100) with the housing (110) removed to better illustrate the adjustable shielding device (101). As shown there, the adjustable shielding device (101) may comprise an iris assembly comprising a plurality of leaflets (102), a first gear (104), and a second gear (106). Generally, the plurality of leaflets (102) may be formed from one or more high magnetic permeability alloy (such as those described above), and may be configured to act as a shielding member which may modify the magnetic field produced by the magnet (111), and may be positioned such that the plurality of leaflets (102) define a central opening (116) through the plurality of leaflets (102) (e.g., as shown in FIG. 1C). The plurality of leaflets (102) may be moveable to adjust a size of the central opening (116), which may in turn alter the amount of shielding provided by the plurality of leaflets (102). Accordingly, the leaflets (102) may act as an iris to move between an open configuration (such as shown in FIG. 1C) and a closed configuration (such as shown in FIG. 1D) to adjust the size of the central opening (116). Adjusting the size of the opening (116) may adjust the surface area of the magnet (111) that is exposed, which may in turn adjust the strength of the magnetic field that passes through the plurality of leaflets (102).

The leaflets (102) may be movable in any suitable manner. In some variations, each leaflet (102) may be attached to the first gear (104) such that rotation of the first gear (104) causes the leaflets (102) to move between open and closed configurations. Each leaflet (102) may be rotatably connected to the first gear (104) (e.g., via a pin joint (128)) and to a portion of the housing (110) (e.g., via a pin joint (140)). Rotation of the first gear (104) in a first direction may cause each leaflet (102) to rotate around the pin joint (140) in a first direction, while rotating the first gear (104) in an opposite direction may rotate each leaflet (102) in an opposite direction. In the variation shown in FIGS. 1A-1D, each leaflet may comprise a main body (118) and a connector (120) connecting the main body (118) to the first gear (104). The main body (118) may have a triangle-like shape, with a first convex side (122), a second concave side (126), and a third side (124) (which is shown in FIGS. 1A-1D as being convex). The concave side (126) may join the first convex side (122) at a first corner (130) and may join the third side (124) at a second corner (132). When the leaflets are rotated toward a closed configuration, the first corner (130) of each leaflet may meet to close off the central opening (116) (as shown in FIG. 1D). When the leaflets are rotated toward an open configuration, the first corner (130) of each leaflet may be drawn toward the second corner (132) of an adjacent leaflet to increase the size of the central opening (116).

The iris assembly may be any suitable iris assembly. While shown in FIGS. 1A-1D as having five leaflets (102), the iris mechanism may comprise any suitable number of leaflets (e.g., two, three, four, five, or six or more leaflets), and each leaflet may have any suitable shape. Additionally, when the leaflets comprise a connector (such as connector (120) discussed above), the connector may be rigidly or pivotably attached to the main body of the leaflet. Additionally, while the connectors (120) are shown above as having an arcuate shape, it should be appreciated that the connectors may have any suitable shape, such as a linear shape or the like. In some variations, one or more leaflets may be configured to at least partially overlap, wherein the amount of overlap between adjacent leaflets may be adjusted to adjust the size of the central opening.

The first gear (104) may be rotated in any suitable manner to rotate the iris assembly between open and closed configurations. For example, in the variation of the magnetic control assembly shown in FIG. 1A, the adjustable shielding device (101) may comprise a second gear (106) and a control (108) connected to the second gear (106). The second gear (106) may be positioned relative to the first gear (104) such that rotation of the second gear (106) also rotates the first gear (104) (e.g., via one or more interlocking teeth as shown in FIGS. 1A-1D, one or more beveled gears including straight, spiral, or hypoid teeth, or the like). While the first gear (104) is shown in FIGS. 1A-1D as being parallel to the second gear (106), it should be appreciated that in some variations these gears may be perpendicular to each other. Additionally, it should be appreciated that one or more intermediate gears may be positioned between the first and second gears, whereby the intermediate gears translate rotation of the second gear (106) into rotation of the first gear (104). In other variations, the first (104) and second gear (104) may be configured in a rack and pinion arrangement. The control (108) (which is shown in FIGS. 1A-1D as comprising an L-shaped rigid member (136) and a grip (138), but may be any suitable structure) may be connected to the second gear (106) such that a user may use the control (108) to rotate the second gear (106) which in turn may rotate the first gear (104). In other variations, a control (108) may be connected directly to the first gear (104), such that the control may be used to rotate the first gear (104) directly. In other variations, the adjustable shielding device (101) may comprise a motor (not shown) configured to rotate one or more of the gears.

Generally, the housing (110) may be configured to hold or otherwise house some or all of the components of the magnetic control assembly (100). While shown in FIG. 1A as housing the components of the adjustable shielding device (100), the housing (110) may also at least partially house the magnet (111). In variations where a control (108) is used to rotate one or more gears, the control (108) may connect to the one or more gears through the housing such that a user may manipulate the control. Additionally or alternative, the housing (100) may comprise an opening (not shown) aligned with the central opening formed by the leaflets (102), which may provide direct access to the magnet (111) through the opening in the housing (100) and the central opening formed by the leaflets (102).

In some variations, the adjustable shielding device (100) may comprise a controller configured to control the shielding provided by the adjustable shielding device (100). For example, in instances where a magnetic device comprises one or more sensors or is otherwise configured to send a signal to the magnetic control assembly (100), the controller may be configured to adjust the shielding provided by the adjustable shielding device (100) in response to data received from the magnetic device. For example, the controller may monitor the strength of the magnetic field monitored by a magnetometer of a magnetic device, or may monitor the pressure sensed by a pressure sensor of the magnetic device, and may compare these values to a desired level or range (which may be pre-set or selected by a user). If the measured values deviate from the range, the controller may be configured to adjust the shielding provided by the adjustable shielding device (100). For example, if the pressure measured by a magnetic device is above a target range or value, the controller may be configured to rotate the iris assembly to decrease the size of the central opening (116), which may reduce the strength of the magnetic field applied to the magnetic device. Alternatively, if the measured pressure is below a target range or value, the controller may be configured to rotate the iris assembly to increase the size of the central opening (116) (e.g., by activating a motor to rotate the first gear (104)), which may increase the strength of the magnetic field applied to the magnetic device. The leaflets may be incrementally and reversibly adjusted until a desired magnetic field strength or pressure is achieved.

In other variations, the controller may be configured to provide feedback to a user regarding the parameters measured by the controller. For example, the controller may comprise a user interface, such as a control panel which may be configured to display information to the operator. In some variations, the user interface may display the data received from the magnetic devices. Additionally or alternatively, the user interface may alert an operator when the parameters measured by the magnetic device deviates from a target value or range. In these instances, the operator may manually adjust the shielding provided by the adjustable shielding device to alter the magnetic field applied to the magnetic device (e.g., by moving a control (108) or running a motor via one or more motor controls).

Figure 2A:
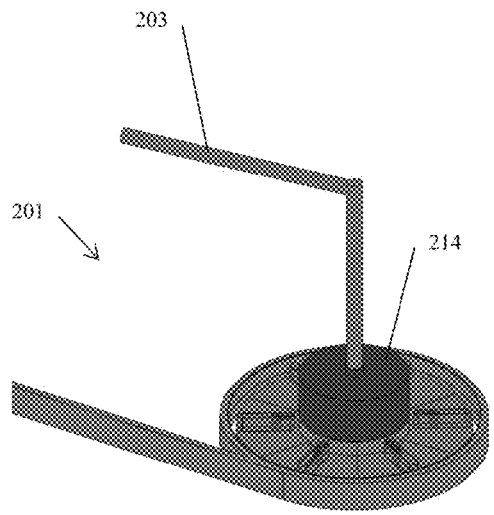
FIG. 2A depicts a perspective view of an illustrative magnetic control assembly having an adjustable shielding device.
Figure 2B:
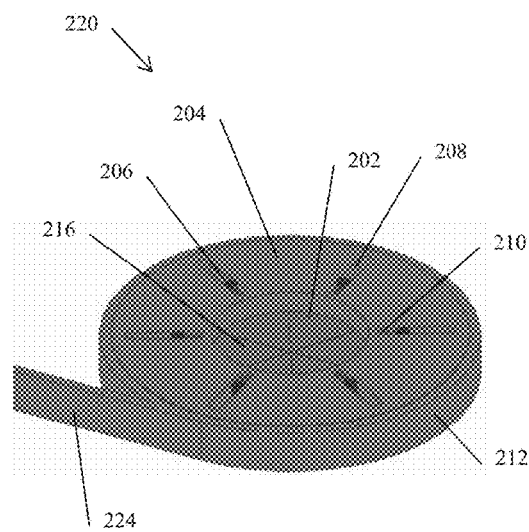
FIGS. 2B and 2C depict a perspective view and a bottom view, respectively, of the assembly of FIG. 2A.

FIG. 2A depicts a perspective view of another illustrative variation of a magnetic control assembly (201) having an adjustable shielding device (200). As shown there, the magnetic control assembly may also comprise a magnet (214) and a mounting device (203), such as discussed in more detail above. FIG. 2B shows a perspective view of the adjustable shielding device (200) with the magnet (214) and mounting device (203) removed. As shown there, the adjustable shielding device (200) may comprise a plurality of leaflets (202) which are slidably attached to a holding plate (204). The holding plate (214) may further comprise an opening (216), and the leaflets (202) may be moveable to selectively block the opening (216). For example, the leaflets (202) may slide toward the opening to block the opening (216) (as shown in FIG. 2B), or may slide away from the opening to at least partially unblock the opening (as shown in a bottom view in FIG. 2C). The magnet (214) may be placed over the opening (216) (as shown in FIG. 2A), and the holding plate (204) and leaflets (202) may be formed from one of the magnetic shielding materials as described above. By increasing or decreasing the proportion of opening (216) that is blocked by the leaflets (202), the adjustable shielding device (200) may control the amount of shielding provided by leaflets (202) and holding plate (204).

The leaflets (202) may be slidably attached to the holding plate (204) in any suitable manner. For example, in the variation shown in FIGS. 2A-2C, the holding plate (204) may comprise a plurality of channels (208), and the leaflets (202) may each comprise a pin (206) extending from the leaflet (202) slidably positioned in a respective channel (208). In some variations, the channels (208) may extend radially from the opening (216) in the holding plate (204), such that the pins (206) and leaflets (202) slide toward and away from the opening (216). In some variations the pins (206) may be configured such that they may not be disengaged from the channel (208) (e.g., the pins (206) may comprise tip portions having a diameter greater than a width of the channel (208) such that the holding plate is held between the tip portions of the pins (206) and the leaflets (202). In some variations, the adjustable shielding device (200) may comprise one or more springs (210) configured to bias the leaflets (202) toward an open configuration (e.g., configured to bias the leaflets (202) away from the opening (216) in the holding plate (204). It should also be appreciated that leaflets (202) may be slidably attached to holding plate (204) by mechanisms other than pins (206).

The leaflets (202) may be moveable relative to the holding plate (204) in any suitable manner. For example, in some variations, the adjustable shielding device (200) may comprise a belt (212) circumferentially positioned around the leaflets (202). A first end of the belt loop (212) may be attached at an end to a leaflet (202) at an attachment point (222) and may be wrapped circumferentially around the remaining leaflets (202). A second end (224) of the belt (212) may be pulled to reduce the circumference of the belt (212) that is wrapped around the leaflets (202). This in turn may cause leaflets (202) to move radially inward as the attached pins (206) move slidably inward along channels (208) (which may also compress springs (210)), which may move the leaflets (202) to block the opening (216) of the holding plate (204). If belt (212) is loosened, the radially inward force on leaflets (202) may be decreased, and springs (210) may push pins (206) radially outward, causing leaflets (202) to move toward an open configuration. The belt (212) may be adjusted to control the amount that the leaflets (202) block the opening (216) in the holding plate (204). The second end of the belt (224) may be moved in any suitable manner. For example, the second end of the belt (224) may be attached to a motor, gear assembly, or other mechanism configured to selectively tighten and loosen the belt (224) to close and open the opening (216).

Figure 2C:
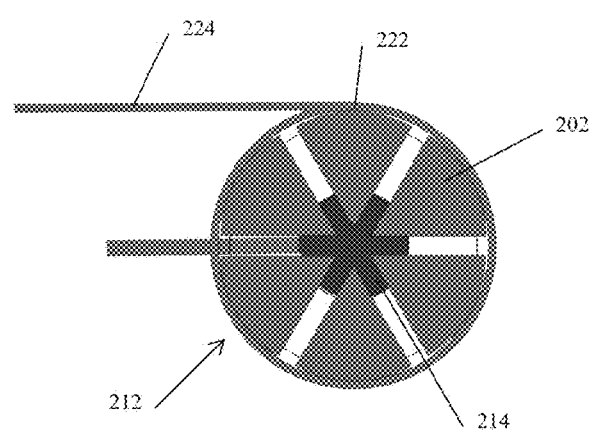

While shown in FIGS. 2A-2C as having six leaflets (206), the adjustable shielding device (200) may comprise any number of leaflets (e.g., two, three, four, five, six, seven, or eight or more leaflets). Generally, each leaflet may have a wedge shape having a wedge angle, and generally the wedge angles of the leaflets add up to 360 degrees to allow the leaflets to form a contiguous shape to entirely block the opening (216). In some variations, each wedge shape has the same shape and wedge angle. For example, the adjustable shielding device may comprise have 2 leaflets each having a 180 degrees wedge angle, 3 leaflets each having a 120 degree wedge angle, 4 leaflets having a 90 degree wedge angle, 5 leaflets having a 72 degree wedge angle, 6 leaflets each having a 60 degree wedge angle (as shown in FIGS. 2A-2C), or the like. In other variations, different leaflets may have different wedge angles. The number of channels (208) of the holding plate (204) may correspond to the number of leaflets (202) (although it should be appreciated that the holding plate may include additional channels for other purposes).

In some variations, the adjustable shielding device (200) may comprise a controller configured to control the shielding provided by the adjustable shielding device (200), such as described above. For example, the controller may be configured to control the positioning of the second end (224) of the belt (e.g., via a motor, or the like) to block or unblock the opening (216) in response to data received from a magnetic device. Additionally or alternatively, the controller may provide information or feedback to the operator, and the operator may control the movement of the belt to selectively alter the shielding provided by the adjustable shielding device (200).

Figure 3A:
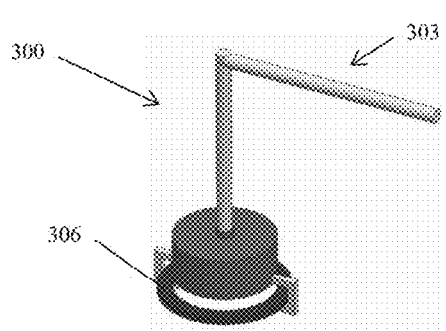
FIGS. 3A-3B depict perspective views of another illustrative magnetic control assembly having an adjustable shielding device.
Figure 3B:
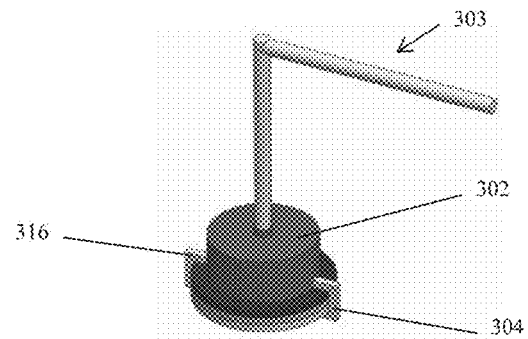

FIGS. 3A-3B depict another illustrative variation of a magnetic control assembly having an adjustable shielding device (300). As shown there, the magnetic control assembly may comprise a magnet (302) and a mounting device (303). The adjustable shielding device (300) may comprise a holder (304) attached to or otherwise fixed relative to magnet (302) and configured to hold one or more shielding plates (306) below the magnet (302). This may position the plates (306) between the magnet (302) and the patient. The plate or plates (306) may be formed from one or more magnetic shielding materials such as described above, and may alter the magnetic field produced by the magnet (302). The specific plates (306) placed within the holder (304) can be changed in order to adjust the magnetic field reaching the magnetic device, as will be described in more detail below.

Figure 3C:
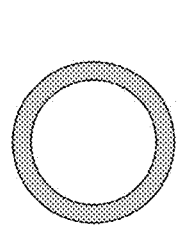
FIGS. 3C-3N depict top views of illustrative interchangeable plates for the adjustable shielding device of FIGS. 3A-3B.
Figure 3F:
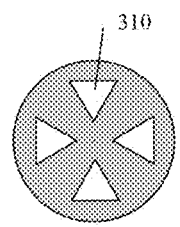
Figure 3I:
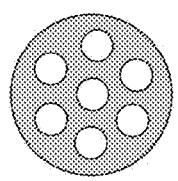
Figure 3L:
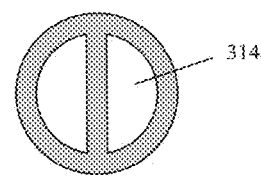
Figure 3D:
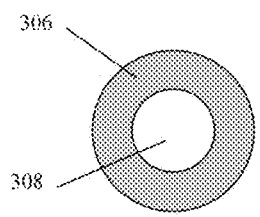
Figure 3G:
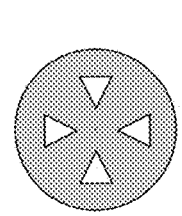
Figure 3J:
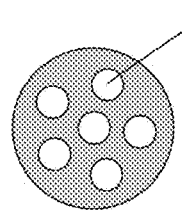
Figure 3M:
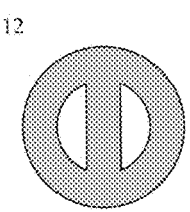
Figure 3E:
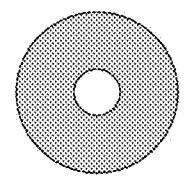
Figure 3H:
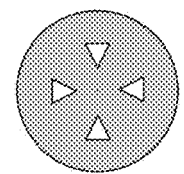
Figure 3K:
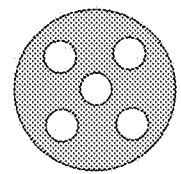
Figure 3N:
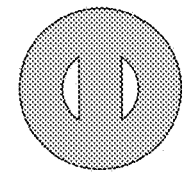

Generally, the shielding plates (306) may have any suitable size and shape (e.g., circular, oval, square, etc.) and include one or more opening extending through the shielding plates. These openings may have any suitable shape (e.g., circles, semi-circles, ovals, rectangles, triangles, teardrops, or any other polygon or irregular shape) and size. For example, FIGS. 3C-3E show variations of shielding plates having circular openings (308) of varying diameters. Generally, the larger the size of the opening, the less of the shielding effect provided by that plate. FIGS. 3F-3H show variations of plates having four triangular openings (310) of varying sizes. Each plate member may have any suitable numbers of openings. For example, FIGS. 3I-3K show variations of plates (306) having seven, six, and five circular openings (312), respectively. FIGS. 3L-3N each show variations of plates (306) having two semi-circular openings (314) of varying sizes.

Generally, the holder (304) may be any structure capable of holding one or more plates (306) relative to the magnet (302). In the variation shown in FIGS. 3A and 3B, the holder (304) may comprise two U-shaped members (316), each having one end attached to magnet (302) at two opposing locations on magnet (302). The holder (304) may comprise be a slot-like frame into which one or more plates (306) can be placed. In some variations, plates (306) may have indentations or protrusions to help secure the plates (306) within holder (304). In some variations, multiple plates (306) may be held simultaneously by holder (304), as shown in FIG. 3B. In some variations, the holder (304) may have an adjustable height, such that in variations in which multiple plates (306) are placed simultaneously into holder (304), the distance between the magnet (302) and the patient is increased. This may further decrease the force provided by the magnet (302) to a magnetic device position in the body.

In some variations in which the magnetic device comprises a sensor, the system may comprise a user interface that may display information from the sensors. The operator may use the information displayed on the user interface to decide whether to exchange or add plates (306) to adjust the exposed surface area of the magnet. In some variations, the user interface may suggest the appropriate plate that should be placed into the holder. If the magnetic field strength or pressure is greater than the desired level, the operator may exchange the plate for one having openings with less total area. For example, the plate shown in FIG. 3C might be exchanged for the plate shown in FIG. 3D. If the magnetic field strength or pressure is less than the desired level, the operator may exchange the plate for one having openings with more total area. For example, the plate shown in FIG. 3K might be exchanged for the plate shown in FIG. 3G.

Figure 4A:
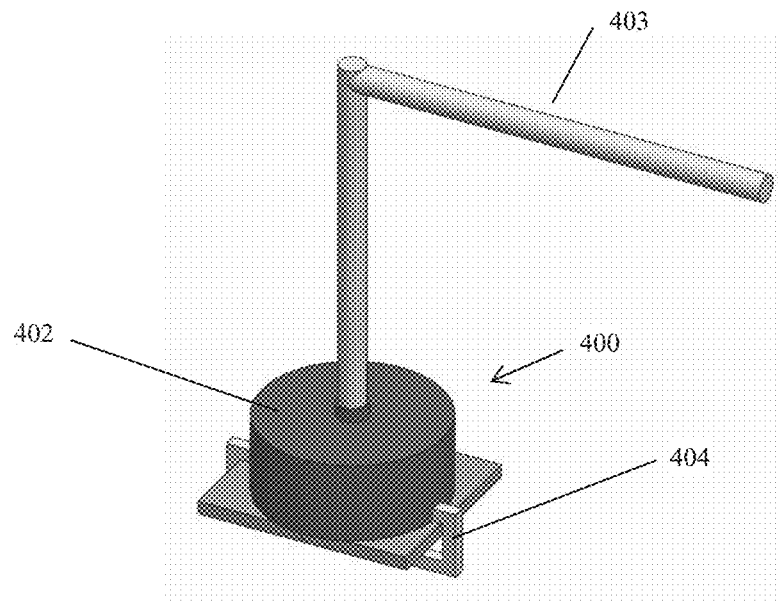
FIGS. 4A-4B depict perspective views of another illustrative magnetic control assembly having an adjustable shielding device.
Figure 4B:
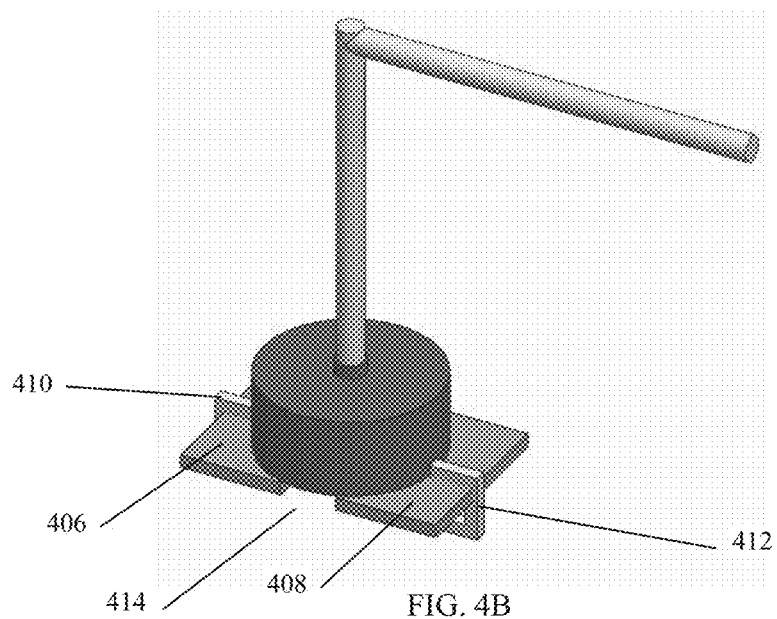

FIGS. 4A-4B depict another illustrative variation of a magnetic control assembly comprising an adjustable shielding device (400). In the magnetic control assembly shown there, the magnetic control assembly may comprise a magnet (402) and a mounting device (403). The adjustable shielding device (400) may comprise a holder (404) that holds two moveable plates (406) and (408). The plates may be formed from one or more magnetic shielding materials, such as described in more detail above. In the variation shown in FIGS. 4A-4B, the holder (404) may be directly attached to the magnet (402), but need not. In other variations the holder (404) may be indirectly connected to the magnet (402) to fix the holder (404) in place relative to the magnet (402). Generally, the plates (406) and (408) may be configured to be moveable toward or away from each other. When moved away from each other (e.g., to an open configuration, as shown in FIG. 4B), a space (414) may be defined between the two plates. Movement of the plates towards each other may reduce the size of the space (414) between the plates. For example, in the variation shown in FIG. 4A-4B, the plates may be moved to a closed configuration (as shown in FIG. 4A) in which the plates form a contiguous structure to close off the space (414). The size of the space (414) may control the shielding provided by the adjustable shielding device (400). For example, when the magnetic control assembly is positioned such that the plates (406) and (408) are positioned between a magnetic device (not shown) and the magnet (402), moving the plates (406) and (408) away from each other may increase the strength of the magnetic field applied to the magnetic device, while moving the plates toward each other may decrease the strength of the magnetic field applied to the magnetic field. In some instances the shielding device (400) may further comprise a controller that receives feedback from a sensor and automatically adjusts the configuration of the moveable plates (406) and (408), such as described in more detail above.

While the plates (406) and (408) are shown in FIGS. 4A and 4B as being rectangular, it should be appreciated that the two moveable plates (406) and (408) may have any suitable shape and size. For example, the two moveable plates (406) and (408) may be semi-circles, circles, ovals, triangles, or the like. It should also be appreciated that in some instances, one or more portions of the two moveable plates (406) and (408) may overlap as the plates move towards each other.

As mentioned above, moveable plates (406) and (408) may be held between magnet (402) and the patient by a holder (404), which may have any suitable configuration. For example, in the variation shown in FIGS. 4A and 4B, the holder (404) may comprise two U-shaped members (410) and (412), which may each be attached to magnet (402) (e.g., at opposing ends of the magnet). The moveable plates (406) and (48) may be attached to the U-shaped members (410) and (412), respectively. In some variations, moveable plates (406) and (408) may have indentations or protrusions to help secure them relative to the U-shaped members (410) and (412), respectively. Additionally or alternatively, U-shaped members (410) and (412) may have clips or slots to help secure moveable plates (406) and (408). The U-shaped members (410) and (412) may be moveable relative to magnet (402) to move the plates (406) and (408), respectively, relative to the magnet (402). For example, in some variations the U-shaped members (410) and (412) may be slidably connected to the magnet (402). In other variations, the U-shaped members (410) and (412) may be configured to have adjustable lengths. The U-shaped members and plates may be moved manually, or using one or more motors (not shown) or the like. It should be appreciated that adjustable shielding device (400) may comprise a locking mechanism to temporarily fix the plates in a specific configuration.

As mentioned above, the adjustable shielding device (400) may be configured to move the plates in response to a signal received from a sensor of a magnetic device, as discussed above. For example, in some variations the U-shaped members (410) and (412) may be moved by a motor, and a the adjustable shielding device may comprise a controller that receives feedback from a sensor, and adjusts the positioning of one or both of the U-shaped members (and with it, the positioning of the moveable plates relative to each other). For example, the controller may monitor the strength of the magnetic field monitored by a magnetometer of a magnetic device, or may monitor the pressure sensed by a pressure sensor of the magnetic device, and may compare these values to a desired level or range (which may be pre-set or selected by a user). If the measured values deviate from the range, the controller may be configured to adjust the shielding provided by the adjustable shielding device (400). For example, if the pressure measured by a magnetic device is above a target range or value (or if a measured magnetic field is above a target strength value or range), the controller may be configured to move the plates (406) and (408) toward each other, which may reduce the strength of the magnetic field applied to the magnetic device. Alternatively, if the measured pressure is below a target range or value (or if a measured magnetic field is below a target strength value or range), the controller may be configured to move the plates (406) and (408) away each other, which may increase the strength of the magnetic field applied to the magnetic device. The plates may be incrementally and reversibly adjusted until a desired magnetic field strength or pressure is achieved.

In other variations, the controller may be configured to provide feedback to a user regarding the parameters measured by the controller. For example, the controller may comprise a user interface, such as a control panel, which may be configured to display information to the operator. In some variations, the user interface may display the data received from the magnetic devices. Additionally or alternatively, the user interface may alert an operator when the parameters measured by the magnetic device deviates from a target value or range. In these instances, the operator may manually adjust the shielding provided by the adjustable shielding device to alter the magnetic field applied to the magnetic device (e.g., by moving the plates (406) and (408) relative to each other).

Distance Adjustment Devices

In some embodiments, the force modulation device may comprise a distance adjustment device configured to adjust a distance between a magnet of the magnetic control assembly and a magnetic device positioned in the body. Because a magnet's magnetic field strength at a given distance from the magnet is inversely proportional to the distance squared, the magnitude of the magnetic field applied by the magnet to a magnetic device can be controlled by adjusting the distance between the magnet and the patient. The distance adjustment devices described here generally comprise one or more expandable elements for controlling the distance between the magnet and the patient, as described in more detail below. In some variations where the system comprises a mounting device, one or more of the one or more expandable elements may be positioned between the magnet and the patient, and the one or more expandable elements may control the distance between the magnet and the patient by moving the magnet and the mounting device relative to the patient. In other variations where the system comprises a mounting device, one or more of the one or more expandable elements may be positioned between the mounting device and the magnet, and the one or more expandable elements may control the distance between the magnet and the patient by moving the magnet relative to the mounting device. In some variations, the distance adjustment device may comprise an automated feedback mechanism to automatically adjust the distance between the magnet and the magnetic device, as described in more detail below.

In some variations, the distance adjustment device may comprise one or more inflatable members. FIGS. 5A-5D depict two such variations of magnetic control assemblies. For example, FIGS. 5A and 5B show a first variation of a magnetic control assembly (501). As shown there, the magnetic control assembly (501) may comprise a magnet (504), a mounting device (514), and a distance adjustment device (500) having an inflatable member (502). The inflatable member (502) may be any suitable inflatable member (e.g., a balloon, inflatable bladder, or the like), and may be selectively inflated and deflated (e.g., by introducing or removing, respectively, one or more gases, liquids, gels, slurries, or solids such as microspheres from the inflatable member). The inflatable member (502) may be attached to or otherwise positioned relative to the magnet (504) such that the inflatable member (502) may be positioned between the magnet (504) and a patient (not shown).

The inflatable member (502) may be inflated from a deflated configuration (as shown in FIG. 5A) to an inflated configuration (as shown in FIG. 5B). As the inflatable member (502) is inflated, the size of the inflatable member (502) increases. If the inflatable member (502) is positioned between the magnet (504) and a magnetic device positioned in the body, inflation of the inflatable member (502) may push the magnet (504) away from the magnetic device, which may increase the distance between the magnet (504) and the magnetic device. This increase in separation distance may reduce the strength of the magnetic field applied to the magnetic device. It should be appreciated that inflation of the inflatable member (502) may move the magnet (504) (e.g., pushing against a counterbalancing force provided by a mounting device (514) to move the magnet (504)) and/or move the magnetic device (e.g., by pushing against a surface of the skin to move the magnetic device positioned under the skin). Conversely, deflation of the inflatable member (502) may reduce the spacing provided by the inflatable member (502), which may increase the force applied to the magnetic device by the magnet (504).

The inflatable member (502) may have any suitable shape. For example, in FIGS. 5A-5B the inflatable member (502) is shown as having a substantially box shape with rounded corners. In other variations, the inflatable member may have a cylindrical or hollow cylindrical shape. FIGS. 5C and 5D show another variation of a magnetic control assembly (521), which may comprise a magnet (524), a mounting device (534), and distance adjustment device (520) comprising an inflatable member (522) having a hollow cylindrical shape. As shown there, the inflatable member (522) may comprise a plurality of individual bladders (530) which may be joined or otherwise connected to form the hollow-cylindrical shape of the inflatable member (522). Generally, inflation of the inflatable member (522) may increase the height of the cylinder (as shown in FIG.

5D), while deflation of the inflation member (522) may decrease the height of the cylinder (as shown in FIG. 5C). This increase and decrease in height may increase and decrease, respectively, the distance between the magnet (524) and a magnetic device (not shown) positioned in the body, as discussed in more detail above.

In some variations, the inflatable member may be configured to at least partially hold a magnet of the magnetic assembly. For example, in the variation of the magnetic control assembly (521) shown in FIGS. 5C and 5D, the inflatable member (522) may comprise an upper portion (532) and a lower portion (536). The interior of the hollow cylindrical inflatable member (522) may comprise a divider (not shown) separating the upper (532) and lower (536) portions, and the upper (532) and lower (536) portions may be separately inflated and deflated. In these variations, the magnet (524) may be placed inside of the upper portion (532) of the inflatable member (522). In some of these variations, when the magnet is placed inside of the upper portion (532) of the inflatable member (522), the upper portion (532) may be inflated to apply pressure to the magnet (524), which may in turn temporarily couple the upper portion (532) of the inflatable member (522) to the magnet (524). The lower portion (536) may be selectively deflated (as shown in FIG. 5C) or inflated (as shown in FIG. 5D) to decrease or increase, respectively, the height of the lower portion (536), which in turn may alter the force applied by the magnet (534) to a device positioned in the body. It should be appreciated that in some variations, the inflatable member (522) may comprise other features to connect the inflatable member (522) to the magnet (524), such as an elastic sleeve, which may be placed over the magnet (524) to couple the inflatable member (522) to the magnet (524).

It should be appreciated that the inflatable members described here may be inflated or deflated using one or more ports. For example, in the variation of the inflatable member (522) shown in FIGS. 5C and 5D, the upper portion (532) and lower portion (534) may each include a port (526) through which one or more gases, fluids, etc. may be introduced into or removed from the inflatable member (522). In some variations, the inflatable members may be inflated or deflated through the same port. In other variations, the inflatable members may be inflated through an inflation port and may be deflated through a deflation port. Additionally, in some variations, the medium used to inflate the inflatable member may have magnetic shielding properties (e.g., the inflatable member may be inflated with a slurry or fluid containing a high magnetic permeability metal alloy, such as described above), which may cause the inflatable member to also act as an adjustable shielding device. In these instances, inflating the inflatable member may both increase the amount of shielding provided by the inflatable member, and may increase the distance between the magnet and a magnetic device positioned in the body. Conversely, deflating the inflatable member may both decrease the amount of shielding provided by the inflatable member, and may decrease the distance between the magnet and a magnetic device positioned in the body. Additionally, the inflatable member may distribute forces applied to the inflatable member (e.g., by the magnet of the magnetic control assembly), which may in turn distribute pressure applied by the inflatable member to the skin. This may reduce damage or irritation to the skin that may occur when a magnetic assembly is pressed against the skin of the patient.

As mentioned above, the inflatable members described above may be inflated or deflated in response to a signal received from a sensor of a magnetic device, as discussed above. For example, in some variations, the inflatable member may be inflated and/or deflated using one or more controllable pumps, valves, combinations thereof, and the like, and the distance adjustment device may comprise a controller configured to control the inflation and deflation of the inflatable member. For example, the controller may monitor the strength of the magnetic field monitored by a magnetometer of a magnetic device, or may monitor the pressure sensed by a pressure sensor of the magnetic device, and may compare these values to a desired level or range (which may be pre-set or selected by a user). If the measured values deviate from the range, the controller may be configured to adjust the inflation of the inflatable member. For example, if the pressure measured by a magnetic device is above a target range or value (or if a measured magnetic field is above a target strength value or range), the controller may be configured to inflate the inflatable member, which may move a magnet away from the magnetic device to reduce the strength of the magnetic field applied to the magnetic device. Alternatively, if the measured pressure is below a target range or value (or if a measured magnetic field is below a target strength value or range), the controller may be configured to deflate the inflatable member, which may decrease the distance between a magnet and the magnetic device, which may increase the strength of the magnetic field applied to the magnetic device. The inflation of the inflatable member may be incrementally and reversibly adjusted until a desired magnetic field strength or pressure is achieved.

In other variations, the controller may be configured to provide feedback to a user regarding the parameters measured by the controller. For example, the controller may comprise a user interface, such as a control panel, which may be configured to display information to the operator. In some variations, the user interface may display the data received from the magnetic devices. Additionally or alternatively, the user interface may alert an operator when the parameters measured by the magnetic device deviates from a target value or range. In these instances, the operator may manually adjust the level of inflation of the inflatable member.

FIGS. 6A-6B and 6E-6F depict additional illustrative variations of a magnetic control assembly (600) comprising a distance adjustment device. As shown there, the magnetic control assembly may comprise a magnet (614), a mounting device (603), and a distance adjustment device comprising a pneumatic cylinder assembly (601). The pneumatic cylinder assembly (601) may comprise one or more pneumatic cylinders (602) (two are shown in the variation in FIGS. 6A-6B and one is shown in the variation in FIGS. 6E-6F, but the pneumatic cylinder assembly may comprise any suitable number of pneumatic cylinders, such as one, two, three, or four or more pneumatic cylinders). The pneumatic cylinders (602) may each comprise a cylinder (604) and a piston (606) slidably positioned in the cylinder (604). The piston (606) may comprise a piston rod (608) which may extend out of the cylinder (604), and may be configured to connect (directly or indirectly) to the magnet (614). Generally, each cylinder (604) may comprise one or more pressure ports (610). In the variation shown in FIGS. 6A-6B, the pressure ports (610) of each piston (606) may be connected to a connecting pipe (612) having a pressure port (616). In these variations, gas or fluid may be introduced into or vented from the pressure port (616) of the connecting pipe (612) to supply or vent gas from the pressure ports (610) of each piston (606). In other variations, each pneumatic cylinder (602) may be individually controlled.

Figure 6E:
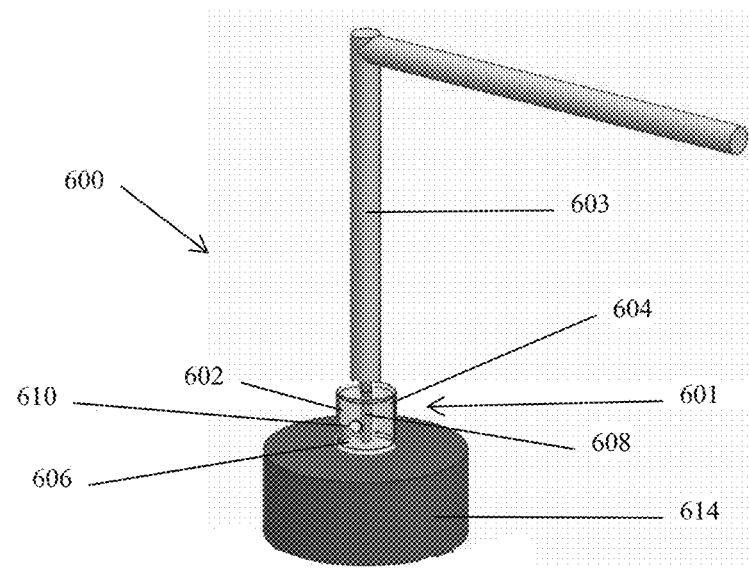
FIGS. 6E-6F depict perspective views of another illustrative magnetic control assembly having the distance adjustment device of FIGS. 6A-6B.
Figure 6F:
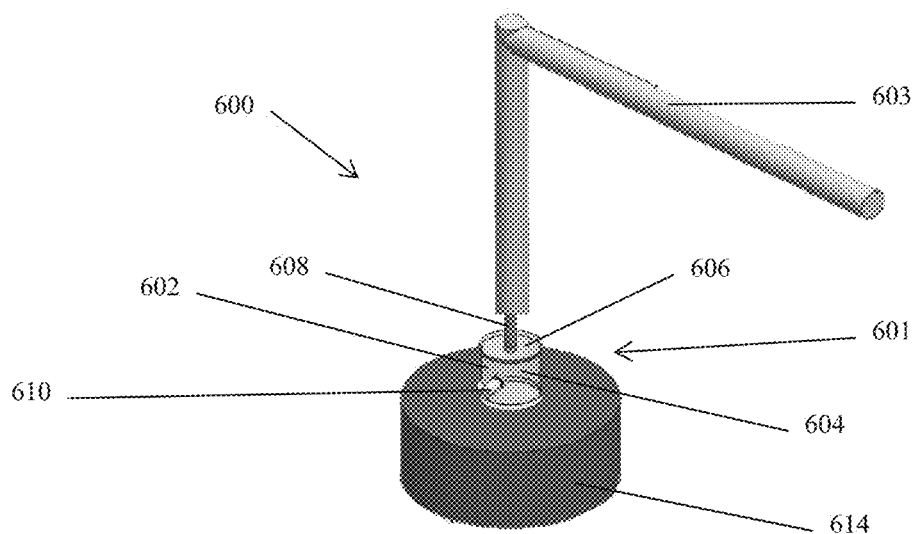

Generally, a compressed gas or fluid may be introduced into the pressure port (610) of each cylinder (604) (e.g., by introducing compressed gas or fluid into the pressure port (616) of the connecting pipe (612)), which may push the piston (606) away from the pressure port (610) and drive the piston rod (608) out of the cylinder (604) (as shown in FIGS. 6B and 6F). In variations where the pneumatic cylinder assembly (601) is located between the magnet (614) and a patient (including a magnetic device (not shown) positioned in the patient), as in FIGS. 6A-6B, as the piston rod (608) is driven out of the cylinder (604), the piston (606) may push the magnet (614) away from the cylinder(s) (604). Movement of the cylinder(s) (604) away from the magnet (614) may increase the distance between the magnetic device and the magnet (614), which may decrease the force applied to the magnetic device by the magnet (614). If the pneumatic cylinder assembly (601) is located between the magnet (614) and the mounting device (603), as in FIGS. 6E-6F, as the piston rod (608) is driven out of the cylinder (604), the piston (606) may push the magnet (614) away from the mounting device (603). Movement of the magnet (614) away from the mounting device (603) may decrease the distance between the magnet (614) and a magnetic device (not shown) positioned in a patient, which may increase the force applied to the magnetic device by the magnet (614).

When the pressure applied to the pressure port (610) is removed, the piston (606) and piston rod (608) may slide back toward the pressure port (610). In variations in which the pneumatic cylinder assembly (601) is located between the magnet (614) and the patient, as in the variation of FIGS. 6A-6B, the movement of the piston(s) (606) and piston rod(s) (608) toward the pressure port(s) (610) may decrease the distance between the cylinder(s) (604) and the magnet (614). This may decrease the distance between the magnet (614) and a magnetic device located in the patient (not shown), which may increase the force applied to the magnetic device by the magnet (614). In variations in which the pneumatic cylinder assembly (601) is located between the magnet (614) and the mounting device (603), as in the variation of FIGS. 6E-6F, the movement of the piston(s) (606) and piston rod(s) (608) toward the pressure port(s) (610) may move the magnet (614) toward the mounting device (603). This may increase the distance between the magnet (614) and a magnetic device located in the patient (not shown), which may decrease the force applied to the magnetic device by the magnet (614).

In some variations, weight of the magnet (614) or pistons (606) may provide a return force that may cause the pistons (606) to move back toward the pressure port (610) when the pressure is lessened. Additionally or alternatively, such as shown in FIG. 6C, the pneumatic cylinder may further comprise a spring (618) positioned in the cylinder (604). The spring (618) may be positioned such that it becomes compressed when pressure applied to the piston (606) moves the piston (606) and piston rod (608) away from pressure port (610). When the pressure is released, spring (618) may decompress and push the piston (606) and piston rod (608) back to their original positions. In other variations, the spring may be positioned such that it becomes stretched when the piston (606) is moved away from the pressure port (610), and may un-stretch when the pressure is removed to pull the piston (606) toward the pressure port (610). In other variations, such as shown in FIG. 6D, a cylinder may comprise a second pressure port (620) in addition to the first pressure port (610). In these variations, when pressure applied through the first pressure port (610) is greater than the pressure applied to the second pressure port (620), the piston (606) may move toward the second pressure port (620). Conversely, when the pressure applied through first pressure port (610) is less than the pressure applied through the second pressure port (620), the piston (606) may move toward the first pressure port (610).

In the above variations, the positioning of the pistons (606) within the cylinders (604) (and thus the distance between the cylinders (604) and the magnet (614) when the pneumatic cylinder assembly (601) is located between the magnet (614) and the patient, or the distance between the magnet (614) and the mounting device (603) when the pneumatic assembly (601) is located between the magnet (614) and the mounting device (603)) may be used to incrementally affect the distance between a magnet (614) and a magnetic device positioned in the body between a compressed configuration (FIGS. 6A and 6E) and an expanded configuration (FIGS. 6B and 6F). When the pneumatic cylinder assembly (601) is positioned between the magnet (614) and a patient, as in the variation in FIGS. 6A-6B, the pneumatic cylinder(s) may directly or indirectly contact the patient. For example, in some variations, the cylinder(s) (604) may be placed directly in contact with the patient. In other variations, the cylinder(s) (604) may be attached to a first base member (such as a plate, cushioned pad, or the like) and the piston rod(s) (608) may be attached to a second base member. One of the base members may be attached to the magnet (614), the other may be positioned in contact with patient (e.g., the patient's abdomen), and the pneumatic cylinder(s) (602) may control the distance between the first and second base members to control the distance between the magnet (614) and the patient. When the pneumatic cylinder assembly (601) is positioned between the magnet (614) and the mounting device (603), as in the variation in FIGS. 6E-6F, the cylinder(s) (604) may be directly or indirectly (e.g., via a base member) attached to the magnet (614), and the piston rod(s) (608) may be directly or indirectly (e.g., via a base member) attached to the mounting device (603). The pneumatic cylinder(s) (602) may control the distance between the magnet (614) and the patient by adjusting the distance between the magnet (614) and the mounting device (603).

In some variations, the pneumatic cylinders may be controlled in response to a signal received from a sensor of a magnetic device, as discussed above. For example, in some variations, pressurized fluid or gas may be supplied to the pneumatic cylinders using one or more pumps or the like, and the distance adjustment device may comprise a controller configured to control the pressure supplied to the pneumatic cylinders. For example, the controller may monitor the strength of the magnetic field monitored by a magnetometer of a magnetic device, or may monitor the pressure sensed by a pressure sensor of the magnetic device, and may compare these values to a desired level or range (which may be pre-set or selected by a user). If the measured values deviate from the range, the controller may be configured to adjust the inflation of the inflatable member.

For example, in variations where the pneumatic cylinder assembly is located between the magnet and the patient, if the pressure measured by a magnetic device is above a target range or value (or if a measured magnetic field is above a target strength value or range), the controller may actuate the pneumatic cylinder(s) to drive the piston rod(s) out of the cylinder(s) as described, which may move a magnet away from the magnetic device to reduce the strength of the magnetic field applied to the magnetic device. Alternatively, if the measured pressure is below a target range or value (or if a measured magnetic field is below a target strength value or range), the controller may actuate the pneumatic cylinder(s) to retract the piston rod(s) into the cylinder(s) as described, which may decrease the distance between a magnet and the magnetic device, which may increase the strength of the magnetic field applied to the magnetic device. The pneumatic cylinders may be incrementally and reversibly adjusted until a desired magnetic field strength or pressure is achieved.

In variations where the pneumatic cylinder assembly is located between the magnet and a mounting device, if the pressure measured by a magnetic device is above a target range or value (or if a measured magnetic field is above a target strength value or range), the controller may actuate the pneumatic cylinder(s) to retract the piston rod(s) into the cylinders as described above, which may move the magnet away from the magnetic device (e.g., toward the mounting device) to reduce the strength of the magnetic field applied to the magnetic device. Alternatively, if the measured pressure is below a target range or value (or if a measured magnetic field is below a target strength value or range), the controller may actuate the pneumatic cylinder(s) to drive the piston rod(s) out of the cylinder(s) as described, which may decrease the distance between the magnet and the magnetic device (and increase the distance between the mounting device and the magnet), which may increase the strength of the magnetic field applied to the magnetic device. The pneumatic cylinders may be incrementally and reversibly adjusted until a desired magnetic field strength or pressure is achieved.

In other variations, the controller may be configured to provide feedback to a user regarding the parameters measured by the controller. For example, the controller may comprise a user interface, such as a control panel, which may be configured to display information to the operator. In some variations, the user interface may display the data received from the magnetic devices. Additionally or alternatively, the user interface may alert an operator when the parameters measured by the magnetic device deviates from a target value or range. In these instances, the operator may manually control the adjustment of the pneumatic cylinders.

FIGS. 7A-7B and FIGS. 7D-E depict additional illustrative variations of magnetic control assemblies comprising a distance adjustment device. As shown there, the magnetic control assembly may comprise a mounting device (709), a magnet (708), and a distance adjustment device comprising a scissor jack or similar linkage assembly (700). As shown there, the scissor jack assembly (700) may comprise a base element (702), a top element (704), and a linkage mechanism (706). In some variations, such as the variation shown in FIGS. 7A-7B, the base element (702) may be placed against a patient (directly or indirectly), while the top element (704) may be connected (directly or indirectly) to the magnet. In other variations, such as the variation shown in FIGS. 7D-7E, the base element (702) may be connected (directly or indirectly) to the magnet (708), while the top element (704) may be connected (directly or indirectly) to the mounting device (709).

Figures 7A, 7B:
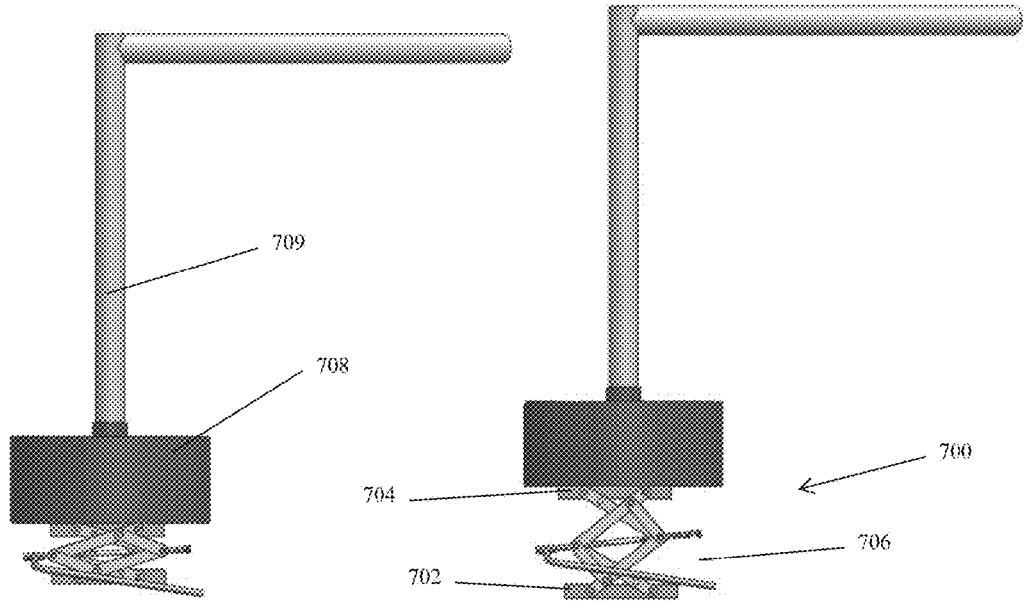
FIGS. 7A-7B depict perspective views of an illustrative magnetic control assembly having a distance adjustment device.
Figure 7C:
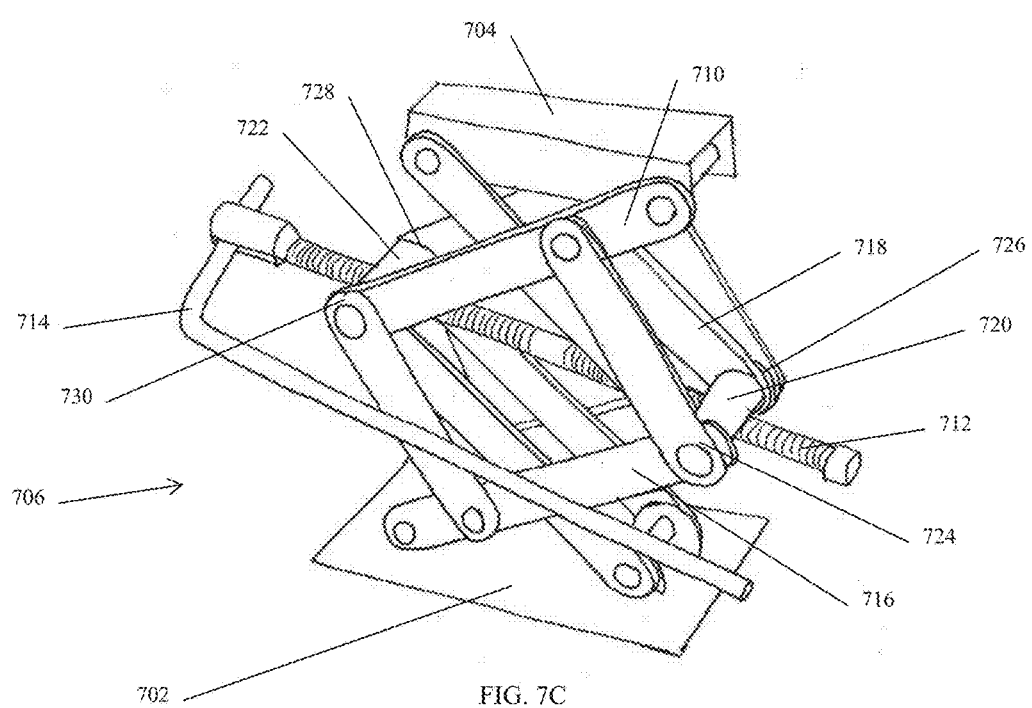
FIG. 7C depicts a perspective view of the distance adjustment device of the assembly in FIGS. 7A-7B.
Figure 7D:
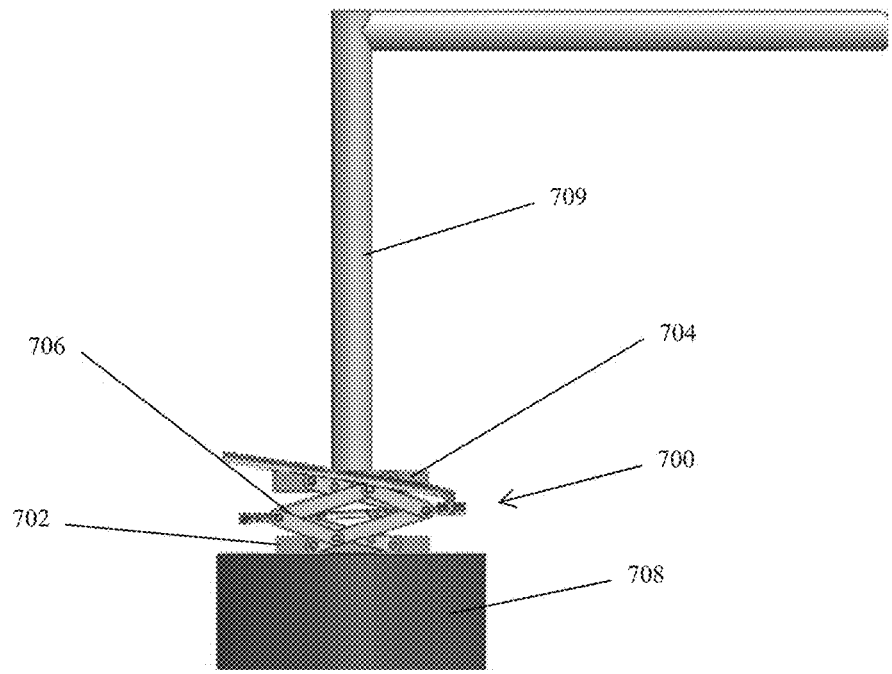
FIGS. 7D-7E depict perspective views of an illustrative magnetic control assembly having the distance adjustment device of FIGS. 7A-7C.
Figure 7E:
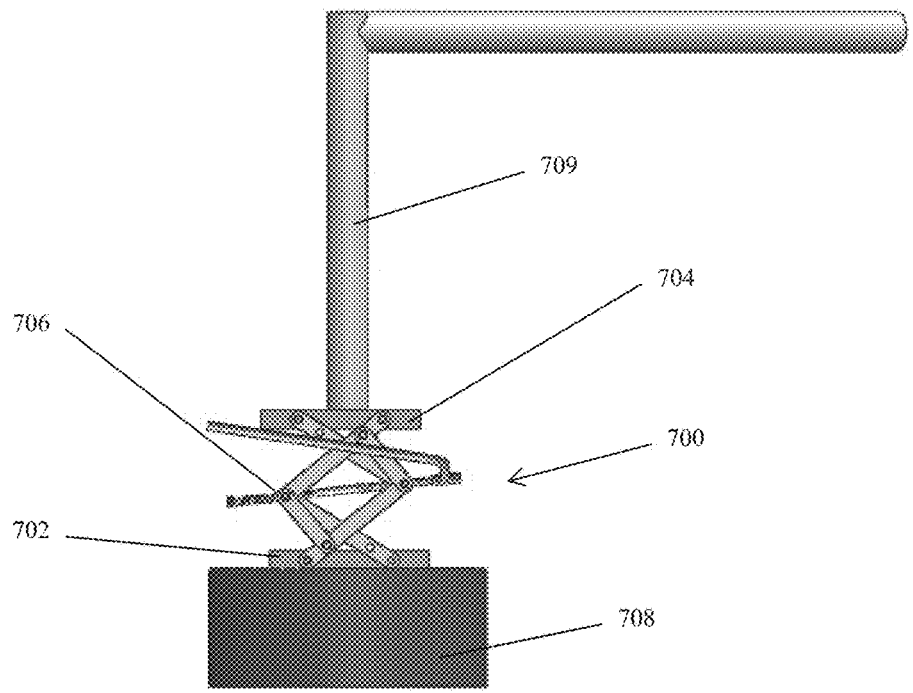

The linkage mechanism (706) may be expanded to increase the distance between the base element (702) and the top element (704), such as shown in FIGS. 7B and 7E. When the distance adjustment device is located between the magnet (708) and the patient, expanding the linkage mechanism (706) may move magnet (708) away from the patient and may decrease the strength of the magnetic field that may reach a magnetic device positioned within the patient. When the distance adjustment device is located between the magnet (708) and the mounting device (709), expanding the linkage mechanism (706) may move the magnet (708) toward the patient and increase the strength of the magnetic field that may reach a magnetic device positioned within the patient.

The linkage mechanism (706) may be compressed to decrease the distance between the base element (702) and the top element (704). When the distance adjustment device is located between the magnet (708) and the patient, compressing the linkage mechanism (706) may move magnet (708) toward the patient and increase the strength of the magnetic field reaching the magnetic device. When the distance adjustment device is located between the magnet (708) and the mounting device (709), compressing the linkage mechanism (706) may move the magnet (708) away from the patient and decrease the strength of the magnetic field that may reach the magnetic device. Individual components of the scissor jack assembly (700) described here will be described in more detail below.

The linkage mechanism (706) is shown in more detail in FIG. 7C. As shown there, it may comprise a plurality of interconnected elongate members (710), a bolt (712), and a crank (714). Generally, the crank (714) may be configured to rotate the bolt (712), and rotation of the bolt (712) may alter the height of the linkage mechanism (706). In the variation shown in FIG. 7C, the elongate members (710) form two six-member linkages (716) and (718). The two six-member linkages are aligned parallel to each other and connected by rods (720) and (722) at pivot joints (724) and (726), and (728) and (730), respectively. The bolt (712) may be axially fixed relative to one of the rods (722) and (720), and may be threaded (712) such that rotation of the bolt (712) moves the fixed rod relative to the unfixed rod. Rotation of the bolt (712) in a first direction may move the first rod (722) toward the second rod (720), which may cause the linkages (716) and (718) to rotate in a manner that increases the distance between the base element (702) and the top element (704). Rotation of the bolt (712) in the opposite direction may move the first rod (722) away from the second rod (720), which may cause the linkages (716) and (718) to rotate in a manner that decreases the distance between the base element (702) and the top element (704). Accordingly, the rotation of the bolt (712) may be controlled to control the distance between the base element (702) and the top element (704). While the crank (714) is shown in FIGS. 7A-7E as rotating the bolt (712), it should be appreciated that in some variations a motor or other control device may be connected to the bolt (712) for rotation thereof. While shown in FIGS. 7A-7E as having a single scissor jack assembly (700), the distance adjustment devices may comprise a plurality of scissor jack or linkage assemblies, which may be moved independently or in a synchronized fashion.

In some variations, the scissor jack assembly may be controlled in response to a signal received from a sensor of a magnetic device, as discussed above. For example, in some variations, the distance adjustment device may comprise a controller configured to control the height of the scissor jack assembly. For example, the controller may monitor the strength of the magnetic field monitored by a magnetometer of a magnetic device, or may monitor the pressure sensed by a pressure sensor of the magnetic device, and may compare these values to a desired level or range (which may be pre-set or selected by a user). If the measured values deviate from the range, the controller may be configured to adjust the height of the scissor jack assembly. For example, if the pressure measured by a magnetic device is above a target range or value (or if a measured magnetic field is above a target strength value or range), the controller may actuate the scissor jack assembly to change the height of the scissor jack assembly. If the scissor jack assembly is located between a magnet and the patient, the controller may actuate the scissor jack assembly to increase the height of the scissor jack assembly, which may move the magnet away from the magnetic device to reduce the strength of the magnetic field applied to the magnetic device. If the scissor jack assembly is located between a magnet and a mounting device, the controller may actuate the scissor jack assembly to decrease the height of the scissor jack assembly, which may move the magnet toward the mounting device and away from the magnetic device to reduce the strength of the magnetic field applied to the magnetic device. If the measured pressure is below a target range or value (or if a measured magnetic field is below a target strength value or range), the controller may actuate the scissor jack assembly to change the height of the scissor jack assembly. If the scissor jack assembly is located between a magnet and the patient, the controller may actuate the scissor jack assembly to decrease the height of the scissor jack assembly, which may decrease the distance between the magnet and the magnetic device, which may increase the strength of the magnetic field applied to the magnetic device. If the scissor jack assembly is located between a magnet and a mounting device, the controller may actuate the scissor jack assembly to increase the height of the scissor jack assembly, which may move the magnet away from the mounting device and toward the magnetic device to increase the strength of the magnetic field applied to the magnetic device. The scissor jack assembly may be incrementally and reversibly adjusted until a desired magnetic field strength or pressure is achieved.

In other variations, the controller may be configured to provide feedback to a user regarding the parameters measured by the controller. For example, the controller may comprise a user interface, such as a control panel, which may be configured to display information to the operator. In some variations, the user interface may display the data received from the magnetic devices. Additionally or alternatively, the user interface may alert an operator when the parameters measured by the magnetic device deviates from a target value or range. In these instances, the operator may manually control the adjustment of the scissor jack assembly, It should be appreciated that the magnetic control assemblies described here may comprise any combination of adjustable shielding devices and/or distance adjustment devices described above.

Methods

Methods for minimally invasive surgery are also described here. Generally, the methods described here comprise positioning a magnetic device (such as any of the magnetic devices described above) in the body of a patient, positioning a magnetic control assembly externally of the patient's body, and manipulating the magnetic device using the magnetic control assembly. In some variations, the magnetic device may be positioned in an abdominal cavity. The magnetic device may be advanced into the body using one or more laparoscopic ports or like. Additionally or alternatively, the magnetic device may be coupled (releasably or permanently) to a tissue (such as a gallbladder, appendix, or the like).

The magnetic control assembly may be any of the magnetic control assemblies described above, and may comprise one or more force-modulation devices. In some variations, the methods further comprise positioning the force-modulation device between a magnet of the magnetic control assembly and the magnetic device, or between a magnet of the magnetic control assembly and a mounting device of a magnetic control assembly, and may further comprise adjusting a force applied to the magnetic device using the force modulation device. In some variations, this may comprise altering the distance between the magnet and the magnetic device using the force modulation device. Additionally or alternatively, this may comprise altering the magnetic field produced by the magnet using an adjustable shielding device.

As discussed in more detail above, the force modulation device may alter the force applied to the magnetic device in response to feedback received by the force modulation device. For example, when the magnetic device comprises a sensor (such as discussed above), the force modulation device may be configured to alter the force applied to the magnetic device based on information received from the sensor. In some of these variations, the force modulation device may comprise a controller configured to automatically adjust the force applied to the magnetic device based on information received from the sensor. By modulating the force applied to the magnetic device, the magnetic control device may control the positioning of the magnetic device relative to the patient while minimizing the risk that the magnetic device will exert too much pressure on the patient's tissue.

Although the foregoing invention has, for the purposes of clarity and understanding, been described in some detail by way of illustration and example, it will be apparent that certain changes and modifications may be practiced, and are intended to fall within the scope of the appended claims. Additionally, it should be appreciated that the devices described here may comprise any combination of device components and features described above.

We claim:

1. A system comprising:
    a magnetic device configured to be positioned in a body of a patient; and
    a magnetic control assembly comprising a magnet configured to generate a magnetic field and apply a magnetic force to the magnetic device and a distance adjustment device located between the magnetic device and the magnet and comprising an expandable member configured to alter a magnitude of the magnetic force applied by the magnet by controlling a distance between the magnet and the patient, and wherein the expandable member comprises an inflatable member.

2. The system of claim 1 wherein the magnetic control assembly further comprises a mounting device.

3. The system of claim 1 wherein the magnetic device comprises a sensor and the distance adjustment device comprises a controller, and wherein the controller is configured to automatically alter the magnitude of the force applied by the magnet in response to information measured by the sensor.

4. A system comprising:
    a magnetic device configured to be positioned in a body of a patient; and
    a magnetic control assembly comprising a magnet configured to generate a magnetic field and apply a magnetic force to the magnetic device and a distance adjustment device located between the magnetic device and the magnet and comprising an expandable member configured to alter a magnitude of the magnetic force applied by the magnet by controlling a distance between the magnet and the patient and by controlling the magnetic field produced by the magnet, and wherein the magnetic control assembly further comprises a mounting device fixed relative to the expandable member, the expandable member configured to alter the magnitude of the magnetic force applied by the magnet by controlling a shielding material disposed in the expandable member.

\* \* \* \* \*